United States Patent [19]

Gasson et al.

[11] Patent Number: 5,158,946
[45] Date of Patent: Oct. 27, 1992

[54] CEPHALOSPORIN DERIVATIVES AND PHARMACEUTICAL COMPOSITIONS

[75] Inventors: Brian C. Gasson; Jeremy D. Hinks, both of Betchworth, England

[73] Assignee: Beecham Group p.l.c., England

[21] Appl. No.: 583,226

[22] Filed: Sep. 14, 1990

[30] Foreign Application Priority Data

Sep. 14, 1989 [GB] United Kingdom ............ 8920793

[51] Int. Cl.$^5$ ............ C07D 501/26; A61K 31/545
[52] U.S. Cl. .................... 514/202; 514/201; 540/221; 540/222; 540/205; 540/301
[58] Field of Search ............ 540/222, 221; 514/202, 514/201

[56] References Cited

U.S. PATENT DOCUMENTS 4,937,330 6/1990 Sacko et al. .................. 540/222

FOREIGN PATENT DOCUMENTS 2941214 3/1980 Fed. Rep. of Germany.

Primary Examiner—Nicholas S. Rizzo
Attorney, Agent, or Firm—Rosenman & Colin

[57] ABSTRACT

$\beta$-Lactam compounds of the formula (I) including pharmaceutically acceptable salts and in vivo hydrolysable esters, processes for their preparation and their use as antibiotics:

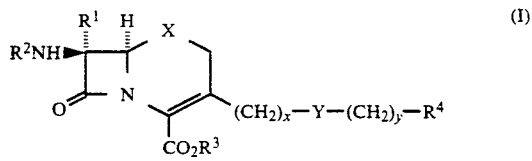

wherein
$R^1$ is hydrogen, methoxy or formamido;
$R^2$ is an acyl group, in particular that of an antibacterially active cephalosporin;
$R^3$ is hydrogen or a readily removable carboxy protecting group (such as a pharmaceutically acceptable in-vivo hydrolysable ester group);
$R^4$ is a $\gamma$- or $\delta$-lactone ring optionally containing one or (where applicable) two endocyclic double bonds, which ring is optionally substituted at any carbon atom by alkyl, dialkylamino, alkoxy, hydroxy, halogen or aryl, which in the case of more than one substituent may be the same or different, or is optionally di-substituted at two adjacent carbon atoms, which are available for substitution, to form an aromatic fused bicyclic system; x and y are independently 0 or 1; X is S, SO, $SO_2$, O or $CH_2$; and Y is O or S.

13 Claims, No Drawings

CEPHALOSPORIN DERIVATIVES AND PHARMACEUTICAL COMPOSITIONS

This invention relates to novel β-lactam containing compounds, their preparation and their use, and in particular to a novel class of cephalosporins. These compounds have antibacterial properties, and therefore are of use in the treatment of bacterial infections in humans and animals caused by a wide range of organisms.

German Offenlegungsschrift, DE 2941214 (Farmitalia Carlo Erba S.p.A.) discloses cephalosporin derivatives of formula (A):

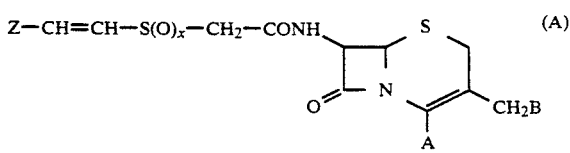

wherein Z is $-CONHNH_2$, $-CONHOH$, $-C(NH)NHR_a$, $-CSNH_2$, $-NHCONHR_a$, $-NHCONHC(NH)NH_2$ or $-CONHCONHR_a$;

A is a free or esterified COOH group;

x is 0, 1 or 2;

B is H, $-OCOMe$ or $-S-Het$, where Het is inter alia, a 5-membered heteromonocyclic ring containing one or more double bonds and one or more heteroatoms selected from N, S and O, the ring being optionally substituted by one or more halogen, $-OH$, $C_{1-6}$alkyl, oxo, $C_{1-6}$alkoxy, trihalomethyl, $-SO_2R_b$, $-NHSO_2R_b$, $-NR_cR_d$, $-(CH_2)_mCO_2R_a$, $-CH=CHCOOR_a$, $-(CH_2)_mSO_3H$, $-CH=CHSO_3H$, $-(CH_2)_mCONR_cR_d$ and $-CH=CHCONR_cR_d$; $R_a$ is H or $C_{1-6}$alkyl; $R_b$ is $C_{1-6}$alkyl; and $R_c$ and $R_d$ are H or $C_{1-6}$alkyl or $-NR_cR_d$ is a 5-membered heteromonocyclic ring which is optionally unsaturated and optionally contains another heteroatom selected from N, S and O; and m is 0 to 3.

Compounds of formula (A) are described as having activity against Gram-positive and Gram-negative bacteria, for use as human or vetinary medicaments (especially for parenteral administration), as disinfectants, or as animal feed additives.

We have now found a particular class of cephalosporins that possesses high antibacterial activity, in particular against Gram-positive organisms, and also shows good parenteral and oral absorption.

The present invention provides a compound of formula (I) or a salt thereof:

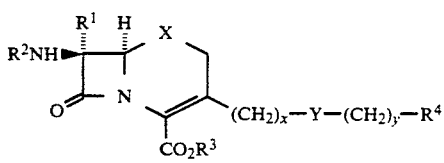

wherein $R^1$ is hydrogen, methoxy or formamido;

$R^2$ is an acyl group, in particular that of an antibacterially active cephalosporin;

$R^3$ is hydrogen or a readily removable carboxy protecting group (such as a pharmaceutically acceptable in-vivo hydrolysable ester group);

$R^4$ is a γ- or δ-lactone ring optionally containing one or (where applicable) two endocyclic double bonds, which ring is optionally substituted at any carbon atom by alkyl, dialkylamino, alkoxy, hydroxy, halogen or aryl, which in the case of more than one substituent may be the same or different, or is optionally di-substituted at two adjacent carbon atoms, which are available for substitution, to form an aromatic fused bicyclic system; x and y are independently 0 or 1; X is S, SO, $SO_2$, O or $CH_2$; and Y is O or S.

The bonding carbon atom of $R^4$ which links the lactone ring to the cephalosporin nucleus may be asymmetric. The present invention includes either stereoisomer, as well as mixtures of both isomers.

In compounds of formula (I) wherein $R^1$ is formamido, the formamido group can exist in conformations wherein the hydrogen atoms of the $-NH-CHO$ moiety are cis- or trans-; of these the cis conformation normally predominates.

As used herein, the term Y-lactone refers to a 5-membered lactone ring bonded via the 3-, 4- or 5-position carbon atom, optionally substituted at the ring carbon atoms as hereinbefore defined, and includes dihydro- and tetrahydro-2-oxofuran rings. The term 6-lactone refers to a 6-membered lactone ring bonded via the 3-, 4-, 5- or 6-position carbon atom, optionally substituted at the ring carbon atoms as hereinbefore defined, and includes dihydro- and tetrahydro-2-oxopyran rings. It will of course be appreciated that a C-4 linked Y-lactone ring, since there are no adjacent carbon atoms available for substitution, cannot form an aromatic fused bicyclic system.

Since the β-lactam antibiotic compounds of the present invention are intended for use as therapeutic agents in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

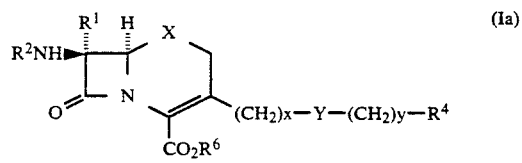

wherein $R^1$, $R^2$, $R^4$, X, Y, x and y are as defined with respect to formula (I) and the group $CO_2R^6$ is $CO_2R^3$ where $CO_2R^3$ is a carboxy group.

Those compounds of the formula (I) wherein $R^3$ is a readily removable carboxy protecting group other than a pharmaceutically acceptable in vivo hydrolysable ester . or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, p-toluenesulphonylethyl, methoxymethyl, a silyl, stannyl or phosphorus-containing group, an oxime radical of formula $-N=CHR^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $C_{1-6}$alkyl, phenyl, $C_{1-6}$alkoxy, hydroxy($C_{1-6}$)alkyl, mercapto($C_{1-6}$)alkyl, halo($C_{1-6}$) alkyl, hydroxy, amino, nitro, carboxy, $C_{1-6}$ alkylcarbonyloxy, alkoxycarbonyl, formyl, or $C_{1-6}$ alkylcarbonyl groups.

The terms 'heterocyclyl' and 'heterocyclic' as used herein include aromatic and non-aromatic, single and fused rings suitably containing up to four hetero-atoms in each ring selected from oxygen, nitrogen and sulphur, which rings may be unsubstituted or substituted by, for example, up to three groups selected from halogen, $C_{1-6}$alkyl, $C_{1-6}$alkoxy, halo($C_{1-6}$)alkyl, hydroxy, carboxy, carboxy salts, carboxy esters such as $C_{1-6}$alkoxycarbonyl, $C_{1-6}$alkoxycarbonyl($C_{1-6}$)alkyl, aryl, and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautomeric forms depending on the nature of the heterocyclyl group; all such tautomeric forms are included within the scope of the invention.

When used herein with respect to variable $R^4$, the term 'aromatic fused bicyclic system' falls within the definition of 'fused heterocyclic ring system' as described above, wherein at least one ring is a 5- or 6-membered lactone ring. Preferably the second ring is a 5- or 6-membered carbocyclic ring.

When used herein the terms 'alkyl' and 'alkoxy' (or 'lower alkyl' and 'lower alkoxy') include straight and branched chain alkyl groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

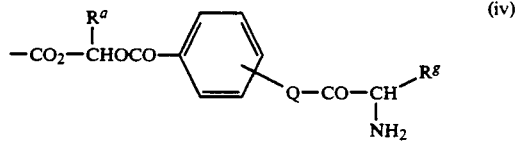

wherein $R^a$ is hydrogen, $C_{1-6}$alkyl, $C_{3-7}$cycloalkyl, methyl, or phenyl, $R^b$ is $C_{1-6}$alkyl, $C_{1-6}$alkoxy, phenyl, benzyl, $C_{3-7}$cycloalkyl, $C_{1-6}$alkyl($C_{3-7}$)cycloalkyl, 1-amino($C_{1-6}$)alkyl, or 1-($C_{1-6}$ alkyl)amino($C_{1-6}$)alkyl; or $R^a$ and $R^b$ together form a 1,2-phenylene group optionally substituted by one or two methoxy groups; $R^c$ represents $C_{1-6}$alkylene optionally substituted with a methyl or ethyl group and $R^d$ and $R^e$ independently represent $C_{1-6}$alkyl; $R^f$ represents $C_{1-6}$alkyl; $R^g$ represents hydrogen or phenyl optionally substituted by up to three groups selected from halogen, $C_{1-6}$alkyl, or $C_{1-6}$alkoxy; and Q is oxygen or NH; $R^h$ is hydrogen or $C_{1-6}$alkyl; $R^i$ is hydrogen, $C_{1-6}$alkyl optionally substituted by halogen, $C_{2-6}$alkenyl, $C_{1-6}$alkoxycarbonyl, aryl or heteroaryl; or $R^h$ and $R^i$ together form $C_{1-6}$alkylene; $R^j$ represents hydrogen, $C_{1-6}$alkyl or $C_{1-6}$alkoxycarbonyl; and $R^k$ represents $C_{1-8}$ alkyl, $C_{1-8}$alkoxy, $C_{1-6}$alkoxy($C_{1-6}$)alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

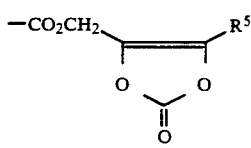

wherein $R^5$ is hydrogen, $C_{1-6}$ alkyl or phenyl.

Suitable pharmaceutically acceptable salts of the carboxy group of the compound of formula (I) include metal salts, e.g. aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (I) or (Ia), the group X may be sulphur or an oxidised sulphur atom, i.e. a sulphoxide (SO) or sulphone (SO) group. When X is a sulphoxide group it will be understood that α- and β-isomers may exist; both such isomers are encompassed within the scope of the present invention.

Preferably X is sulphur.
Preferably Y is sulphur.
Suitably x is 0 and y is 0 or 1, or x is 1 and y is 0.
Advantageously, $R^1$ is hydrogen.
Suitable acyl groups $R^2$ include those of formulae (a)–(f):

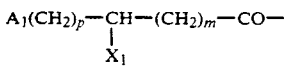  (a)

  (b)

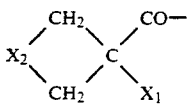  (c)

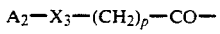  (d)

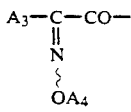  (e)

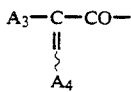  (f)

wherein p is 0, 1 or 2; m is 0, 1 or 2; $A_1$ is $C_{1-6}$ alkyl, substituted $C_{1-6}$alkyl, $C_{3-6}$cycloalkyl, cyclohexenyl, cyclohexadienyl, an aromatic (including heteroaromatic) group, such as phenyl, substituted phenyl, thienyl, pyridyl, or an optionally substituted thiazolyl group, a $C_{1-6}$alkylthio group or $C_{1-6}$ alkyloxy; $X_1$ is a hydrogen or halogen atom, a carboxylic acid, carboxylic ester, sulphonic acid, azido, tetrazolyl, hydroxy, acyloxy, amino ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —$CH_2OCH_2$—, —$CH_2SCH_2$- or alkylene group; $X_3$ is an oxygen or sulphur atom; $A_3$ is an aryl or heteroaryl group such as phenyl, substituted phenyl or aminothiazolyl in which the amino group is optionally protected; and $A_4$ is hydrogen, $C_{1-6}$alkyl, $C_{3-8}$cycloalkyl, $C_{3-8}$cycloalkyl($C_{1-6}$)alkyl, $C_{1-6}$ alkoxycarbonyl($C_{1-6}$) alkyl, $C_{2-6}$alkenyl, carboxy($C_{1-6}$)alkyl, $C_{2-6}$alkynyl, aryl, or $C_{1-6}$alkyl substituted by up to three aryl groups.

The term 'heteroaryl' as used herein means a heteroaromatic heterocyclic ring or ring system, suitably having 5 or 6 ring atoms in each ring.

Suitably when $R^2$ is a group (a), $A_1$ is $C_{1-6}$alkyl, $C_{3-6}$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group. In an example of $R^2$ when a group of formula (a), $A_1$ is phenyl, $X_1$ is hydrogen and p and m are 0.

Alternatively when $R^2$ is a group of formula (e), suitable values for the group $A_3$ include those commonly found in antibacterially active cephalosporins containing a hydroxyimino or substituted hydroxyimino group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, furan-2-yl, thien-2-yl, 2-(2-chloroacetamido)thiazol-4-yl, 2-tritylaminothiazol-4-yl, 5-amino-1,2,4-thiadiazol-3-yl and 4-aminopyrimid-2-yl.

In compounds of formula (Ia), a particularly preferred group for $A_3$ is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Examples of $R^4$ groups include 2,5-dihydro-2-oxofuran-5-yl, 2,5-dihydro-2-oxofuran-4-yl, 2,5-dihydro-2-oxofuran-3-yl, 2-oxotetrahydrofuran-3-yl and 2-oxo-2H-pyran-4-yl derivatives, each of which is optionally substituted by $C_{1-6}$alkyl, for example methyl, or halogen, for example chlorine.

Certain compounds of the invention include an amino group which may be protected. Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$alkyl, $C_{1-4}$alkoxy, trifluoromethyl, halogen, or nitro; $C_{1-4}$alkoxycarbonyl; benzyloxycarbonyl or trityl substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) and pharmaceutically acceptable salts and in-vivo hydrolysable esters thereof include the following:

Sodium 7β-[2-(2-Aminothiazol-4-yl)-2-(Z)-methoxyiminoacetamido]-3-(2,5-dihydro-2-oxofuran-4-ylmethylthio)ceph-3-em-4-carboxylate;

Sodium 7β-[2-(2-Aminothiazol-4-yl)-2-(Z)-methoxyiminoacetamido]-3-(2,5-dihydro-2-oxofuran-4-ylthio)ceph-3-em-4-carboxylate;

Sodium 7β-[2-(2-Aminothiazol-4-yl)-2-(Z)-methoxyiminoacetamido]-3-(2,5-dihydro-3-methyl-2-oxofuran-5-yloxy)ceph-3-em-4-carboxylate;

Sodium 7β-[2-(2-Aminothiazol-4-yl)-2-(Z)-methoxyiminoacetamido]-3-(6-methyl-2-oxo-2H-pyran-4-ylthio)ceph-3-em-4-carboxylate;

Sodium 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate;

7β-[2-(2-Aminothiazol-4-yl)-2-(Z)-hydroxyiminoacetamido]-3-(2,5-dihydro-2-oxofuran-4-ylthiomethyl)ceph-3-em-4-carboxylic acid;

Sodium 7β-[2-(2-Aminothiazol-4-yl)-2-(Z)-methoxyiminoacetamido]-3-(2,5-dihydro-2-oxofuran-3-ylmethylthio)ceph-3-em-4-carboxylate;

7β-[2-(2-Aminothiazol-4-yl)-2-(Z)-hydroxyiminoacetamido]-3-(2,5-dihydro-2-oxofuran-3-ylmethylthio)ceph-3-em-4-carboxylic acid;

Sodium 7β-[2-(2-Aminothiazol-4-yl)-2-(Z)-methoxyiminoacetamido]-3-(2-oxotetrahydrofuran-3-ylthio)-ceph-3-em-4-carboxylate;

Pivaloyloxymethyl-7β-[2-(2-Aminothiazol-4-yl)-2-(Z)-methoxyiminoacetamido]-3-(2,5-dihydro-2-oxofuran-3-yl-methylthio)ceph-3-em-4-carboxylate;

Pivaloyloxymethyl 7β-[2-(2-Aminothiazol-4-yl)-2-(Z)-methoxyiminoacetamido]-3-(2-oxotetrahydrofuran-3-ylthio)ceph-3-em-4-carboxylate;

7β-[2-(2-Aminothiazol-4-yl)-2-(Z)-hydroxyiminoacetamido]-3-(2,5-dihydro-2-oxofuran-4-ylmethylthio)ceph-3-em-4-carboxylic acid;

Sodium 7β-[2-(2-Aminothiazol-4-yl)-2-(Z)-methoxyiminoacetamido]-3(3-chloro-2,5-dihydro-2-oxofuran-4-ylthiomethyl)ceph-3-em-4-carboxylate;

Sodium 7β-[2-(2-Aminothiazol-4-yl)-2-(Z)-methoxyiminoacetamido]-3-(6-methyl-2-oxo-2H-pyran-4-ylthiomethyl)ceph-3-em-4-carboxylate;

Sodium 7β-[2-(2-Aminothiazol-4-yl)-2-(Z)-methoxyiminoacetamido]-3-(2-oxo-2H-pyran-4-ylthiomethyl)ceph-3-em-4-carboxylate;

7β-[2-(2-Aminothiazol-4-yl)-2-(Z)-carboxymethoxyiminoacetamido]-3-(2,5-dihydro-2-oxofuran-4-ylthiomethyl)ceph-3-em-4-carboxylic acid, disodium salt;

7β-[2-(2-Aminothiazol-4-yl)-2-(Z)-hydroxyiminoacetamido]-3-(6-methyl-2-oxo-2H-pyran-4-ylthiomethyl)ceph-3-em-4-carboxylic acid;

Pivaloyloxymethyl 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate;

Pivaloyloxymethyl 7β-[2-(2-Aminothiazol-4-yl)-2-(Z)-methoxyiminoacetamido]-3-(2,5-dihydro-2-oxofuran-4-ylthio)ceph-3-em-4-carboxylate;

Pivaloyloxymethyl 7β-[2-(2-Aminothiazol-4-yl)-2-(Z)-methoxyiminoacetamido]-3-(3-chloro-2,5-dihydro-2-oxofuran-4-ylthiomethyl)ceph-3-em-4-carboxylate;

Pivaloyloxymethyl 7β-[2-(2-Aminothiazol-4-yl)-2-(Z)-methoxyiminoacetamido]-3-(2-oxo-2H-pyran-4-ylthiomethyl)ceph-3-em-4-carboxylate; and Sodium 7β-[2-(2-Aminothiazol-4-yl)-2-(Z)-methoxyiminoacetamido]-3-(2,5-dihydro-2-oxofuran-4-ylmethyloxy)ceph-3-em-4-carboxylate The present invention further provides a process for the preparation of a compound of formula (I), which process comprises treating a compound of formula (II) or a salt thereof:

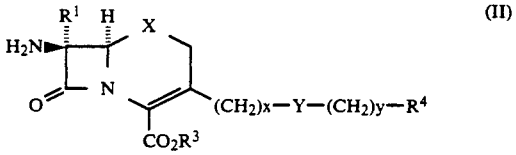

wherein $R^1$, $R^3$, $R^4$, X, Y, x and y are as hereinbefore defined, wherein any reactive groups may be protected, and wherein the amino group is optionally substituted with a group which permits acylation to take place; with an N-acylating derivative of an acid of formula (III):

$R^2OH$      (III)

wherein $R^2$ is as defined with respect to formula (I) and wherein any reactive groups may be protected; and thereafter, if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) reducing any endocyclic double bond within $R^4$;
vi) converting the product into a salt.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —P.R$^8$R$^9$ wherein R$^8$ is an alkyl, haloalkyl, aryl, aralkyl, alkoxy, haloalkyl, aryl, aralkyl, alkoxy, haloalkoxy, aryloxy, aralkyloxy or dialkylamino group, R$^9$ is the same as R$^8$ or is halogen or R$^8$ and R$^9$ together form a ring; suitable such phosphorus groups being —P(OC$_2$H$_5$)$_2$, —P(C$_2$H$_5$)$_2$,

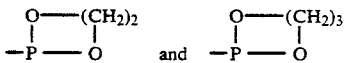

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis(trimethylsilyl)acetamide, N,O-bis(trimethylsilyl)trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°–60° C., preferably 40°–50° C.

The above process may optionally be carried out in the presence of a small quantity, for example 0.1 equivalents, of a silyl halide, for example a tri(C$_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, a tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a (C$_{1-6}$)-1,2-alkylene oxide such as ethylene oxide or propylene oxide. The acylation reaction may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (e.g. chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example BBr$_3$ —C$_6$H$_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

The optional reduction step, the optional conversion of R$^2$ to a different R$^2$, CO$_2$R$^3$ to a different CO$_2$R$^3$ and X to a different X, and the optional formation of a salt, may be carried out using methods well known in the art of cephalosporin and penicillin chemistry.

For example, when the group X is S, SO, or SO$_2$, the group X may be converted into a different group X by methods of oxidation or reduction well known in the art of cephalosporin and penicillin synthesis, as described, for example, in European Patent Application Publication No. 0 114 752. For example, sulphoxides (in which X is SO) may be prepared from the corresponding sulphide (in which X is S) by oxidation with a suitable oxidising agent, for example an organic peracid such as m-chloroperbenzoic acid.

A reduction step is generally effected by process of catalytic hydrogenation in the presence of a suitable catalyst or combination thereof.

In the process described hereinabove, and in the process described hereinbelow, it may be necessary to remove protecting groups. Deprotection may be carried out by any convenient method known in the art such that unwanted side reactions are minimised. Separation of unwanted by-products may be carried out using standard methods.

Compounds of formula (II) are novel compounds and as such form part of the invention. Compounds of formula (II) may be prepared by removal of $R^2$ from compounds of formula (I) prepared by the process described hereinbelow.

In a further process of the invention, compounds of formula (I) may be prepared by treating a compound of formula (IV):

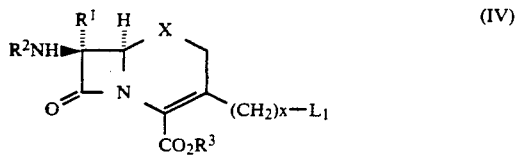

wherein X, $R^1$, $R^2$, x and $R^3$ are as hereinbefore defined and $L_1$ is a Y-group precursor (or a leaving group), with a compound of formula (V):

wherein $L_2$ is a leaving group (or a Y-group precursor) and $R^4$ and y are as hereinbefore defined; and thereafter if necessary or desired, carrying out one or more of the following steps:
 i) removing any protecting groups;
 ii) converting the group $CO_2R^3$ into a different group $CO_2R^3$;
 iii) converting the group $R^2$ into a different group $R^2$;
 iv) converting the group X into a different group X;
 v) reducing any endocyclic double bond within $R^4$;
 vi) converting the product into a salt.

Where $L_1$ in the compound of formula (IV) is a Y-group precursor, suitably the corresponding thiol group, $L_2$ in the compound of formula (V) may be a leaving group, for example a halogen leaving group such as bromo. The reaction may be carried out under standard conditions for nucleophilic substitution reactions, typically in an inert solvent at room temperature or with heating, as dictated by the lability of the leaving group, $L_2$.

Alternatively, where x is 0 and Y is oxygen, $L_2$ may be a hydroxyl group and the reaction may be carried out under 'Mitsunobu' conditions in the presence of triphenylphosphine and diethyl azodicarboxylate.

Where $L_1$ is a leaving group, $L_2$ is suitably a Y-group precursor such as thiol. A typical leaving group $L_1$ is mesyloxy or a halogen group such as chloro and the reaction may be carried out at ambient temperature in an inert solvent optionally in the presence of a base, for example a tertiary amine.

A reaction in which $L_1$ is a leaving group and $L_2$ is a Y-group precursor may also be carried out under 'Mitsunobu' conditions by reacting a compound of formula (IV) in which x is 1 and $L_1$ is hydroxy with a compound of formula (V) in which y is 0 and $L_2$ is an oxo group.

Compounds of formula (IV) in which $L_1$ is a hydroxyl group or a thiol group are known compounds or may be prepared from known compounds. Compounds of formula (IV) in which x is 0 or 1 and $L_1$ is —OH or —SH may be prepared using procedures described by R. Scartazzini and H. Bickel, Helv. Chim. Acta., 57, 1919-34, (1974); E. M. Gordon and C. M. Cimarusti, Tett. Lett., 16. 1359, (1977) and GB Patent 1 516 655. Alternatively a compound of formula (IV) in which x is 0 and $L_1$ is the Y-group precursor, —SH, may be prepared from the corresponding compound in which $L_1$ is a leaving group such as mesyloxy, by reaction with sodium bisulphide, or a leaving group such as methoxy, by reaction with sodium bisulphide in the presence of benzyltrimethyl ammonium chloride and 1,8-diazabicyclo[5.4.0]undec-7-ene.

Compounds of formula (IV) in which $L_1$ is a leaving group, for example mesyloxy or halogen may be prepared by standard methodology from the corresponding compound in which $L_1$ is hydroxy.

Compounds of formula (V) are either known compounds or may be prepared from known starting materials by standard methods in the art of lactone chemistry.

It should be noted that in processes of this invention $\beta^2$-cephems, for example compounds of formula (IV), may function as intermediates, in the synthetic sequences.

Subsequent isomerisation steps by methods well known in cephalosporin chemistry will provide the $\Delta^3$-cephems of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles, which may include edible oils for example almond oil, oily esters for example esters of glycerine, propylene glycol, glycerine, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions ar prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a $\beta$-lactamase inhibitor may be employed.

Advantageously, the compositions also comprise a compound of formula (VIII) or a pharmaceutically acceptable salt or ester thereof:

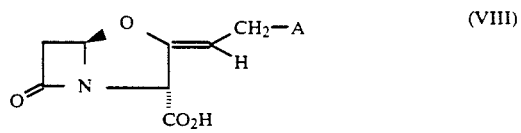

(VIII)

wherein
A is hydroxyl, substituted hydroxyl, thiol, substituted thiol, amino, mono- or di-hydrocarbyl-substituted amino, or mono- or di-acylamino.

A further advantageous composition comprises a compound of formula (Ia) or a pharmaceutically acceptable salt or in vivo hydrolysable ester thereof together with a compound of formula (IX) or a pharmaceutically acceptable salt or in vivo hydrolysable ester thereof:

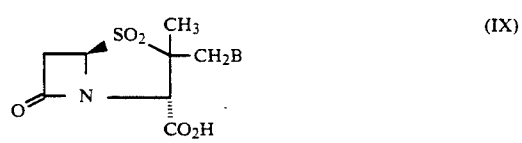

(IX)

wherein
B represents hydrogen or chloro.

Further suitable $\beta$-lactamase inhibitors include $6\beta$-bromopenicillanic acid and pharmaceutically acceptable salts and in vivo hydrolysable esters thereof and $6\beta$-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a $\beta$-lactamase inhibitory amount of a $\beta$-lactamase inhibitor are formulated in a conventional manner using techniques and procedures per se known in the art.

The present invention provides a compound of formula (Ia) or a pharmaceutically acceptable salt or in vivo hydrolysable ester thereof, for use as a therapeutic agent.

The present invention further provides a compound of formula (Ia) or a pharmaceutically acceptable salt or in vivo hydrolysable ester thereof, for use in the treatment of bacterial infections.

The present invention also includes a method of treating bacterial infections in humans and animals which comprises the administration of a therapeutically effective amount of an antibiotic compound of this invention of the formula (Ia) or a pharmaceutically acceptable salt or in vivo hydrolysable ester thereof.

In addition, the present invention includes the use of a compound of formula (Ia) or a pharmaceutically acceptable salt or in vivo hydrolysable ester thereof, for the manufacture of a medicament for the treatment of bacterial infections.

The antibiotic compounds of the present invention are active against a wide range of organisms including both Gram-negative organisms and Gram-positive organisms.

The following Examples illustrate the preparation of the compounds of the present invention and the following biological data illustrate the activity of compounds of the invention in the form of M.I.C. results against a sample *E. coli* organism (NCTC 10418) and a sample *S. aureus* organism (*S. aureus* Oxford).

EXAMPLE 1

Sodium 7β-2-(2-Aminothiazol-4-yl)-2-(Z)-methoxyiminoacetamido]-3-(2,5-dihydro-2-oxofuran-4-ylmethylthio)ceph-3-em-4-carboxylate a) Diphenylmethyl 3-Mercapto-7β-phenylacetamidoceph-3-em-4-carboxylate

Sodium bisulphide (240 mg) was added to a stirred solution of diphenylmethyl 3-methylsulphonyloxy-7β-phenylacetamidoceph-3-em-4-carboxylate (800 mg) in dimethylformamide (10 mls). The mixture was stirred at room temperature for 20 mins. and then partitioned between ethyl acetate and 1N hydrochloric acid. The organic phase was washed successively with 1N hydrochloric acid, twice with water and finally with brine. The solution was dried over magnesium sulphate, evaporated, and dried under vacuum to give a yellow amorphous solid (602 mg), $\nu_{max}$ (nujol) 3270, 2540, 1765 and 1665 cm$^{-1}$; $\delta_H$ [(CD$_3$)$_2$SO] 3.54 (1H, d, J 13.9Hz), 3.60 (1H, d, J14.0Hz), 3.78 (1H, d, J 16.8Hz), 3.87 (1H, d, J 16.8Hz), 5.21 (1H, d, J 4.5Hz) 5.61 (1H, dd, J 4.5 and 8.3Hz), 6.86 (1H, s) 7.2–7.65 (15H, m), 9.14 (1H, d, J 8.3Hz); [mass spectrum :+ve ion (3 NOBA, Na$^+$) MNa$^+$, 539]. The material was used without further purification.

b) Diphenymethyl 3-(2,5-Dihydro-2-oxofuran-4-yl-methylthio)-7β-phenylacetamidoceph-3-em-4-carboxylate N,N-Diisopropylethylamine (0.15 ml) was added to a stirred solution of diphenylmethyl-3-mercapto-7β-phenylacetamidoceph-3-em-4-carboxylate (500 mg) and 4-bromomethyl-2(5H)-furanone$^1$ (200 mg) in tetrahydrofuran (10 ml). After stirring at room temperature for 90 mins. the mixture was partitioned between ethyl acetate and aqueous citric acid solution. The organic phase was separated and washed three times with water, then brine, dried over magnesium sulphate and evaporated. The title compound (474 mg) was isolated by column chromatography of the residue using gradient elution (Kieselgel 1:1 ethyl acetate:hexane going to neat ethyl acetate), m.p. 172°–176° C. from ethyl acetate/hexane. (Found: C, 64.24; H, 4.69; N, 4.51; S, 10.48; C$_{33}$H$_{28}$N$_2$O$_6$S$_2$ requires; C, 64.69; H, 4.61; N, 4.57; S, 10.47); $\nu_{max}$ (CHCl$_3$) 3400, 1785, 1750, 1680 cm$^{-1}$. $\delta_H$ (CDC13) 3.23 ($^1$H, d, J 17.0Hz), 3.38 (1H, d, J 17.1Hz), 3.41 (H, d, J 15.2Hz), 3.53 (1H, d, J 15.1Hz), 3.66 (2H, s), 4.62 (2H, s), 4.98 (1H, d, J 4.6Hz), 5.76 (1H, dd, J 4.6 and 8.8Hz), 5.89 (1H, s), 6.56 (1H, d, J 8.8Hz) 6.91 (1H, s) 7.2–7.4 (15H, m).

c) Diphenylmethyl 7β-Amino-3-(2,5-dihydro-2-oxofuran-4-ylmethylthio)-ceph -3-em-4-carboxylate A stirred solution of diphenylmethyl 3-(2,5-dihydro-2-oxofuran-4-ylmethylthio) -7β-phenylacetamidoceph-3-em-4-carboxylate (520 mg) in dry dichloromethane (8 ml) was cooled to −20° C., then N-methylmorpholine (0.202 ml) was added followed by a solution of phosphorous pentachloride in dichloromethane (7.2 ml of a solution containing 40 mg ml$^{-1}$). The solution was stirred at −15° to −20° C. for 30 mins., then methanol (1.8 ml) was added and the mixture stirred at room temperature for 30 mins. Water (2.5 ml) was then added and the mixture vigorously stirred for a further 30 mins. The dichloromethane was then evaporated on a rotary evaporator and the residue partitioned between ethyl acetate and water. The pH of the aqueous phase was adjusted to 6.0 with saturated sodium bicarbonate solution and the organic phase was separated, washed with water, then brine, dried over magnesium sulphate and evaporated. The title compound (333 mg) was isolated by column chromatography of the residue (Kieselgel, ethyl acetate as eluent). $\nu_{max}$ (CHCl$_3$) 1780 and 1750 cm$^{-1}$; $\delta_H$ (CDCl$_3$) 1.86 (2H, broad s), 3.42 (1H, d, J 17.4Hz), 3.48 (1H, d, J 15.0Hz), 3.60 (1H, d, J 17.4Hz), 3.65 (1H, d, J 15.0Hz), 4.60 (2H, s), 4.78 (1H, d, J 5.1Hz), 4.95 (1H, d, J 5.1Hz), 5.89 (1H, s), 6.99 (1H, s), 7.2–7.5 (10H, m).

d) Diphenylmethyl 3-(2,5-Dihydro-2-oxofuran-4-yl-methylthio)-7β-[2-(2-tritylaminothiazol-4-yl)-2-(Z)-methoxyiminoacetamido]ceph-3-em-4-carboxylate A stirred solution of 2-(2-triylaminothiazol-4-yl)-2-(Z)-methoxyiminoacetic acid hydrochloride (359 mg) and N,N-diisopropylethylamine (0.265 ml) in dry dimethylformamide (2 ml) was cooled to −55° to −60° C. and methanesulphonyl chloride (0.058 ml) was added. The mixture was stirred at the same temperature for 30 mins and then a solution of diphenylmethyl 7-β-amino-3-(2,5-dihydro-2-oxofuran-4-ylmethylthio) ceph-3-em-4-carboxylate (333 mg) in dimethylformamide (4 ml) was added followed by pyridine (0.061 ml). The mixture was then stirred at 0° C. for 90 mins. The mixture was then partitioned between ethyl acetate and sodium bicarbonate solution, the organic phase was washed successively with water, citric acid solution, three times with water, and finally with brine. The solution was dried over magnesium sulphate and evaporated. The title compound (469 mg) was obtained by column chromatography of the residue using gradient elution (Kieselgel 1:1 hexane:ethyl acetate going to ethyl acetate). $\nu_{max}$ (CHCl$_3$) 3400 1785, 1750 and 1685 cm$^{-1}$; $\delta_H$(CDCl$_3$) 3.43 (1H,d, J 17.4Hz), 3.53 (1H, d, J 15.3Hz) 3.54 (1H, d, J 17.4Hz), 3.66 (1H, d, J 15.3Hz), 4.08 (3H, s), 4.64 (2H, s), 5.09 (1H, d, J 4.8Hz), 5.87–5.95 (1H, m), 5.91 (1H, s), 6.75 (1H, s), 6.88 (1H, d, J 7.2), 6.97 (1H, s), 7.02 (1H, s), 7.2–7.5 (25H, m).

e) Sodium 7β-[2-(2-Aminothiazol-4-yl)-2-(Z)-methoxyiminoacetamido]-3-(2,5-dihydro-2-oxofuran-4-ylmethylthio)ceph-3-em-4-carboxylate Diphenylmethyl 3-(2,5-dihydro-2-oxofuran-4-ylmethylthio) -7β-[2-(2-tritylaminothiazol-4-yl)-2-(Z)-methoxyiminoacetamido]ceph-3-em-4-carboxylate (469 mg) was dissolved in 98% formic acid (5 ml) and 1N hydrochloric acid (0.4 ml) was added and the mixture stirred at room temperature for 30 mins. Concentrated hydrochloric acid (0.4 ml) was then added and the mixture stirred for a further 60 mins. Toluene was then added to the mixture and the solvents removed on a rotary evaporator, this procedure was repeated twice more. The residue was stirred with toluene and water and the pH of the aqueous phase was adjusted to 6 with sodium bicarbonate solution. Solid material was filtered off and the aqueous phase separated and evaporated. The product was purified by chromatography on HP20SS eluting with water with increasing proportions of acetone. Fractions containing product were combined, evaporated and the residue dissolved in water (15 ml) and the solution freeze-dried to give the title product (152 mg), $\nu_{max}$ (KBr) 1741 (br), 1669 and 1609 cm$^{-1}$; $\delta_H$ [(CD$_3$)$_2$SO] 3.42 (1H, d, J 16.9Hz), 3.58 (1H, d, J 16.9Hz), 3.72 (1H, d, J 15.5Hz), 3.83 (3H, s), 3.84 (1H, d, J 15.1Hz), 5.00 (1H, d, J 17.5Hz), 5.01 (1H, d, J 4.9Hz), 5.16 (1H, d, J 17.8Hz), 5.58 (1H, dd, J 4.9 and 8.1Hz), 6.15 (1H, s), 6.72 (1H s), 7.25 (2H, s), 9.62 (1H, d, J 8.2Hz); [mass spectrum: +ve ion (3 NOBA, Na$^+$) M Na$^+$ 556].

EXAMPLE 2

Sodium 7β[-2-(2-Aminothiazol-4-yl)-2-(Z)-methoxyiminoacetamido]-3-(2,5-dihydro-2-oxofuran-4-ylthio)-ceph-3-em-4-carboxylate a) 4-Mercapto-2(5H)furanone

Phosphorus pentasulphide (440 mg) was added to a stirred suspension of tetronic acid (1.0 g) in 1,4-dioxan, and the mixture heated to 85° C. for 3 hours. The mixture was cooled and partitioned between water and chloroform. The chloroform layer was separated and the aqueous phase extracted twice more with chloroform. The combined chloroform solution was washed with water, then brine, dried over magnesium sulphate and evaporated. The title compound (98 mg) was isolated by column chromatography using gradient elution (Kieselgel, ethyl acetate going to 10% acetic acid in ethyl acetate as eluent). $\nu_{max}$ (CHCl$_3$) 3570, 1780, 1745 and 1590 cm$^{-1}$; $\delta_H$(CDCl$_3$) 3.80 (1H, br.s), 4.93 (2H, d, J 2Hz), 6.08 (1H, t, J=2Hz).

b) Diphenylmethyl 3-(2,5-Dihydro-2-oxofuran-4-ylthio)-7β-phenylacetamidoceph-3-em-4-carboxylate N,N-Diisopropylethylamine (0.2 ml) was added to a stirred solution of diphenylmethyl 3-methyl sulphonyloxy-7β-phenylacetamidoceph-3-em-4-carboxylate (614 mg) and 4-mercapto-2(5H) furanone (174 mg) in dimethylformamide (10 ml). The mixture was stirred at room temperature for 2 hours and then partitioned between ethyl acetate and 1N hydrochloric acid. The organic phase was washed succesively with 1N hydrochloric acid, water, sodium bicarbonate solution, water and brine. The solution was dried over magnesium sulphate and evaporated. The title compound (204 mg) was isolated by repeated chromatography of the residue using gradient elution (Kieselgel, 2:1 going to 2:3 hexane:ethyl acetate). $\nu_{max}$ (CHCl$_3$) 3400, 1790, 1742, and 1680 cm$^{-1}$; $\delta_H$ (CDCl$_3$) 3.32 (1H, d, J 18.4Hz), 3.62 (1H, d, J 15.9Hz), 3.68 (1H, d, J 18.2Hz), 3.70 (1H, d, J 16Hz), 4.29 (1H, dd, J 12 and 16.7Hz), 4.59 (1H, dd, J 1.4 and 16.6Hz) 5.05 (1H, d, J 5.2Hz), 5.66 (1H, s), 5.94 (1H, dd, J 5.1 and 9.1 Hz), 6.23 (1H, d, J 9.0Hz), 7.02 (1H, s), 7.2–7.5 (15H, m).

c) Diphenylmethyl 7β-Amino-3-(2,5-dihydro-2-oxo-furan-4-ylthio)ceph-3-em-4-carboxylate A stirred solution of diphenylmethyl 3-(2.5-dihydro-2-oxofuran-4-ylthio) -7β-phenylacetamidoceph-3-em-4-carboxylate (348 mg) in dichloromethane (4.8 ml) was cooled to −15° C. to −20° C. and N-methylmorpholine (0.131 ml) was added, followed by a solution of phosphorus pentachloride in dichloromethane (4.65 ml of a solution containing 40 mg ml$^{-1}$). The mixture was stirred at the same temperature for 30 mins. and then methanol (1.2 ml) was added and the mixture stirred at room temperature for 30 mins. Sufficient water and ethyl acetate were then added to enable the mixture to stir vigorously, and stirring was continued for 1½ hours. Most of the organic solvents were then removed on a rotary evaporator and the residue was stirred with water and ethyl acetate and the pH of the aqueous phase was adjusted to 6 with aqueous ammonia. The organic phase was separated, washed with water and brine, dried over magnesium sulphate and evaporated. The title compound (162 mg) was obtained by column chromatography of the residue (Kieselgel 1:1 hexane:ethyl acetate going to neat ethyl acetate as eluent. $\nu_{max}$(nujol) 3410, 1770, and 1735 cm$^{-1}$. $\delta_H$ (CDCl$_3$) 1.82 (2H, s), 3.35 (1H, d, J 18.2Hz), 3.72 (1H, d, J 18.3Hz), 4.27 (1H, dd, J 1.1 and 16.5Hz), 4.59 (1H, dd, J 1.2 and 16.5Hz), 4.87 (1H, d, J 5.3Hz), 5.05 (1H, d, J 5.4Hz), 5.70 (1H, s), 7.05 (1H, s), 7.2–7.4 (10H, m).

d) Diphenylmethyl 3-(2,5-Dihydro-2-oxofuran-4-ylthio)-7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (179 mg) in dimethylformamide (1 ml) was cooled to −55° C. to −60° C. and N,N-diisopropylethylamine (0.13 ml) was added followed by methanesulphonyl chloride (0.029 ml). The mixture was stirred at the same temperature for 30 mins and then a solution of diphenylmethyl 7β-amino-3-(2,5-dihydro-2-oxofuran-4-ylthio) ceph-3-em-4-carboxylate (162 mg) in dimethylformamide (2 ml) was added followed by pyridine (0.03 ml). The mixture was then stirred at 0° C. for 1½ hours, and then partitioned between ethyl acetate and aqueous sodium bicarbonate. The organic phase was washed successively with water, citric acid solution, twice with water, and finally brine. The solution was dried over magnesium sulphate and evaporated. The title compound (256 mg) was isolated by column chromatography of the residue (Kieselgel 1:1 hexane:ethyl acetate going to neat ethyl acetate). $\nu_{max}$ (CHCl$_3$) 3400, 1795, 1780, 1740, and 1685 cm$^{-1}$; $\delta_H$(CDCl$_3$) 3.36 (1H, d, J 18.3Hz), 3.73 (1H, d, J 18.2Hz), 4.10 (3H, s), 4.30 (1H, d, J 16.6Hz), 4.60 (1H, d, J 16.6Hz), 5.16 (1H, d, J 5.0Hz), 5.70 (1H, s), 6.02 (1H, dd, J 5.1 and 8.7Hz), 6.72 (1H, s), 6.88 (1H, d, J 13.4Hz), 7.04 (1H, s), 7.2–7.5 (15H, m).

e) Sodium 7β-2-(2-Aminothiazol-4-yl)-2-(Z)-methoxyiminoacetamido]-3-(2,5-dihydro-2-oxofuran-4-ylthio)ceph-3-em-4-carboxylate Diphenylmethyl 3-(2,5 dihydro-2-oxofuran-4-ylthio)-7β-[2-(2-tritylaminothiazol -4-yl)-2-(Z)-methoxyiminoacetamido]ceph-3-em-4-carboxylate (256 mg) was dissolved in 98% formic acid (5 ml) and 1N hydrochloric acid (0.28 ml) and water (0.28 ml) were added. The mixture was stirred at room temperature for 30 mins. and then concentrated hydrochloric acid (0.2 ml) was added and the mixture stirred for a further 50 mins. The solid was filtered off and the filter cake washed with 90% formic acid. The filtrate was diluted with toluene and the solvents evaporated on a rotary evaporator. Toluene was evaporated from the residue twice more. The residue was stirred with toluene and water and the pH of the aqueous phase was adjusted to 6 with sodium bicarbonate solution. The aqueous phase was separated and evaporated. The product was isolated by HP20SS chromatography of the residue using water with increasing proportions of acetone as eluent. Fractions containing product were combined, evaporated and the residue dissolved in water (15 ml) and freeze dried to give the title compound (69 mg). $\upsilon_{max}$ (KBr) 1773, 1734, 1617 cm$^{-1}$; $\delta_H[(CD_3)_2SO]$ 3.36 (1H, d, J 16.6Hz), 3.83 (1H, d, J 16.4Hz), 3.84 (3H, s), 4.90 (1H, d, J 16.9Hz), 5.15 (1H, d, J 5.0Hz), 5.15 (1H, d, J 16.9Hz), 5.69 (1H, dd, J 5.0 and 8.1Hz), 5.91 (1H, s), 6.72 (1H, s), 7.25 (2H, s), 9.66 (1H, d, J 8.2Hz); [mass spectrum: +ve ion (thioglycerol) MNa+ 542].

EXAMPLE 3

Sodium
7β-[2-(2-Aminothiazol-4-yl)-2-(Z)-methoxyiminoacetamido]-3-(2,5-dihydro-3-methyl-2-oxofuran-5-yloxy)ceph-3-em-4-carboxylate. Isomers a and b (a) Diphenylmethyl
3-(2,5-Dihydro-3-methyl-2-oxofuran-5-yloxy)-7β-phenylacetamido-ceph-3-em-4-carboxylate Diethyl azodicarboxylate (0.32 ml) was added to a stirred solution of diphenylmethyl 3-hydroxy-7β-phenylacetamidoceph-3-em-4-carboxylate (996 mg), 5-hydroxy-3-methylbutenolide$^2$ (228 g) and triphenylphosphine (524 mg) in tetrahydrofuran (40 ml). The solution was evaporated and column chromatography of the residue using gradient elution (Kieselgel, 2:1 going to 1:1 hexane: ethyl acetate) gave a mixture of isomers containing 1,2-dicarbethoxyhydrazine. The product was dissolved in a 1:1 mixture of 60°-80° petroleum ether and chloroform and the solid filtered off. The filtrate was evaporated and column chromatography (Kieselgel 2:1 hexane: ethyl acetate) gave pure samples of each isomer plus mixed fractions. Repeated chromatography of the mixed fractions gave further pure samples of each isomer. Thus were obtained:

Isomer a (222 mg) $\upsilon_{max}$(CHCl$_3$), 3400, 1780, 1725 and 1680 cm$^{-1}$; $\delta_H$(CDCl$_3$) 1.90 (3H, m), 3.54 (2H, s), 3.66 (2H, s), 4.98 (1H, d, J 4Hz), 5.7–6.05 (2H, m), 6.4–6.75 (2H, m), 6.98 (1H, s), 7.3–7.5 (15H, m).

Isomer B (314 mg). $\upsilon_{max}$(CHCl$_3$), 3400, 1775, 1725, and 1675 cm$^{-1}$; $\delta$(CDCl$_3$) 1.90 (3H, m), 3.28 (1H, d, J 18Hz), 3.62 (2H, s), 3.72 (1H, d, J 18Hz), 5.01 (1H, d, J 5Hz), 5.7–6.0 (2H, m), 6.65 (1H, m), 6.86 (1H, d, J 9Hz), 7.01 (1H, s), 7.3–7.5 (15H, m).

(b) Diphenylmethyl
7β-Amino-3-(2,5-dihydro-3-methyl-2-oxofuran-5-yloxy) ceph-3-em-4-carboxylate, hydrochloride. Isomer a.

A stirred solution of diphenylmethyl 3-(2,5-dihydro-3-methyl-2-oxofuran-5-yloxy) -7β-phenylacetamidoceph-3-em-4-carboxylate (isomer a) (222 mg) in dichloromethane (3.5 ml) was cooled to −15° C. and N-methylmorpholine (0.08 ml) was added followed by a solution of phosphorus pentachloride in dichloromethane (3.0 ml of a solution containing 40 mg ml$^{-1}$). The mixture was stirred at −15° C. for 0.5 h and then methanol (0.7 ml) was added and the mixture stirred at room temperature for 0.5 h. Water (1.3 ml) was then added and the mixture vigorously stirred for 0.75 h. The solvent was then evaporated and the residue triturated with ether and cold water. The solid was filtered off then washed with ether, then cold water and finally dried under vacuum to give the desired product (145 mg). $\upsilon_{max}$(nujol) 1775 and 1700 cm$^{-1}$.

(c) Diphenylmethyl
3-(2,5-Dihydro-3-methyl-2-oxofuran-5-yloxy) -7β-[2-(2-tritylaminothiazol-4-yl)-2-(Z)-methoxyiminoacetamido]ceph-3-em-4-carboxylate. Isomer a.

A stirred mixture of 2-(2-tritylaminothiazol-4-yl)-2-(Z)-methoxyiminoacetic acid hydrochloride (145 mg) and N,N-diisopropylethylamine (0.108 ml) in dimethylformamide (1 ml) was cooled to −55° C. to −60° and methanesulphonyl chloride (0.024 ml) was added. The mixture was stirred at the same temperature for 0.5 h, and then diphenylmethyl 7β-amino-3-(2,5-dihydro-3-methyl-2-oxofuran-5-yloxy) ceph-3-em-4-carboxylate hydrochloride (isomer a) and pyridine (0.051 ml) were added. The mixture was then stirred at 0° for 1 h. The mixture was then partitioned between water and ethyl acetate and the organic phase was washed with water, sodium bicarbonate solution, water and brine. The solution was dried over magnesium sulphate and evaporated. The product (132 mg) was isolated by column chromatography of the residue using gradient elution (Kieselgel, 1:1 hexane:ethyl acetate going to neat ethyl acetate). $\upsilon_{max}$(nujol) 3390, 1780, 1720 and 1680 cm$^{-1}$; $\delta$(CDCl$_3$) 1.89 (3H, m), 3.60 (1H, d, J 18.9Hz), 3.70 (1H, d, J 18.9Hz), 4.09 (3H, s), 5.07 (1H, d, J 4.7Hz), 5.93 (1H, dd, J 4.8 and 8.9Hz), 6.00 (1H, m), 6.57 (1H, m), 6.74 (1H, s), 6.86 (1H, d, J 9.0Hz), 6.91 (1H, s), 7.04 (1H, s), 7.1–7.6 (25H, m).

(d) Sodium
7β-[2-(2-Aminothiazol-4-yl)-2-(Z)-methoxyiminoacetamido]-3-L$_{2,5}$-dihydro-3-methyl-2-oxofuran-5-yloxy) ceph-3-em-4-carboxylate. Isomer a.

Diphenylmethyl 3-(2,5-dihydro-3-methyl-2-oxofuran-5-yloxy) -7β-[2-(2-tritylaminothiazol-4-yl)-2-(Z)-methoxyiminoacetamido]ceph-3-em-4-carboxylate (isomer a) (132 mg) was stirred in trifluoroacetic acid (3 ml) at 0° C. for 0.5 h. Toluene was added and the solvent removed on a rotary evaporator, and the process repeated once more. The residue was partitioned between toluene and water and the pH of the aqueous phase was adjusted to 6.5 with sodium bicarbonate solution. The mixture was filtered through Celite and the aqueous phase separated and evaporated to low volume. The product was isolated by HP20SS chromatography (water with increasing proportions of acetone as eluent). Fractions containing product were combined, evaporated and the residue dissolved in water (ca 3 ml) and freeze-dried to give 13 mg of product. $\upsilon_{max}$(KBr) 1763 and 1611 cm$^{-1}$; $\delta[(CD_3)_2SO]$ 2.50 (3H, m), 3.84 (3H, s), 4.99 (1H, d, J 4.8Hz), 5.52 (1H, dd, J 4.5 and 8.1Hz), 6.57 (1H, t, J 1.3Hz), 6.75 (1H, s), 7.18 (1H, t, J 1.4Hz), 7.23 (2H, s), 9.54 (1H, d, J 8.1Hz).

(e) Diphenylmethyl
7β-Amino-3-(2,5-dihydro-3-methyl-2-oxofuran-5-yloxy) ceph-3-em-4-carboxylate, hydrochloride. Isomer b A stirred solution of diphenylmethyl 3-(2,5-dihydro-3-methyl-2-oxofuran-5-yloxy) -7β-phenylacetamidoceph-3-em-4-carboxylate (isomer b) (314 mg) in dichloromethane (5 ml) was cooled to −15° C. and N-methylmorpholine (0.11 ml) was added followed by a solution of phosphorus pentachloride in dichloromethane (4.2 ml of a solution containing 40 mg ml$^{-1}$). The solution was stirred at −15° C. for 0.5 h and then methanol (1 ml) was added and the mixture stirred at room temperature for 0.5 h. Water (1.8 ml) was then added and the mixture vigorously stirred for 0.75 h. Most of the solvents were then removed on a rotary evaporator and the residue triturated with ether and water. The solid was filtered off and washed with a little ether and water and dried under vacuum to give 92 mg of product. $v_{max}$(nujol) 1780 and 1705 cm$^{-1}$.

(f) Diphenylmethyl 3-(2,5-Dihydro-3-methyl-2-oxofuran-5-yloxy) -7β-[2-(2-tritylaminothiazol-4-yl)-2-(Z)-methoxyiminoacetamido]ceph-3-em-4-carboxylate. Isomer b.

A stirred mixture of 2-(2-tritylaminothiazol-4-yl)-2-(Z)-methoxyiminoacetic acid hydrochloride (100 mg) and N,N-diisopropylethylamine (0.067 ml) in dimethylformamide was cooled to −55° to −60° C. and methanesulphonyl chloride (0.016 ml) was added. The mixture was stirred at the same temperature for 0.5 h and then diphenylmethyl 7β-amino-3-(2,5-dihydro-3-methyl-2-oxofuran-5-yloxy) ceph-3-em-4-carboxylate hydrochloride (isomer b) (90 mg) and N,N diisopropylethylamine (0.067 ml) were added. The mixture was then stirred for 1 h. at 0° C. The mixture was then partitioned between ethyl acetate and water, and the organic phase was washed with sodium bicarbonate solution, water and brine. The solution was dried over magnesium sulphate and evaporated. The product (90 mg) was isolated by column chromatography of the residue using gradient elution (Kieselgel 3:1 going to 1:1 hexane:ethyl acetate). $v_{max}$(CHCl$_3$) 3390, 1780, 1720 and 1680 cm$^{-1}$; δ(CDCl$_3$) 1.89 (3H, m), 3.38 (1H, d, J 18.5Hz), 3.74 (1H, d, J 18.5Hz), 4.08 (3H, s), 5.10 (1H, d, J 4.8Hz), 5.76 (1H, m), 5.89 (1H, dd, J 4.8 and 8.8Hz), 6.52 (1H, m), 6.74 (1H, s), 6.84 (1H, d, J 8.7Hz), 6.97 (1H, s), 7.0–7.5 (26H, m).

(g) Sodium 7β-[2-(2-Aminothiazol-4-yl)-2-(Z)-methoxyiminoacetamido]-3-(2,5-dihydro-3-methyl-2-oxofuran-5-yloxy) ceph-3-em-4-carboxylate. Isomer b Diphenylmethyl 3-(2,5-dihydro-3-methyl-2-oxofuran-5-yloxy -7β-[2-(2-tritylaminothiazol-4-yl)-2-(Z)-methoxyiminoacetamido]ceph-3-em-4-carboxylate (isomer b) (90 mg) was dissolved in trifluoroacetic acid (2 ml) and stirred for 0.5 h at 0°. Toluene was added and the solvents removed on a rotary evaporator, and this procedure was repeated once more. The residue was stirred with water and toluene and the pH of the aqueous phase adjusted to 6.5 with sodium bicarbonate solution. The mixture was filtered and the aqueous phase evaporated. The product was purified by HP20SS chromatography (water with increasing proportions of acetone as eluent). Fractions containing product were combined and evaporated, and the residue dissolved in water (3 ml) and freeze dried to give the product (9.8 mg). $v_{max}$(KBr) 1763 and 1611 cm$^{-1}$; δ[(CD$_3$)$_2$SO] 2.50 (3H, m), 3.14 (1H, d, J 17.2Hz), 3.55 (1H, d, J 17.3Hz), 3.83 (3H, s), 5.01 (1H, d, J 4.8Hz), 5.51 (1H, dd, J 4.7 and 8.2Hz), 6.22 (1H, m), 6.73 (1H, s), 7.23 (2H, s), 7.25 (1H, m), 9.56 (1H, d, J 7.2Hz).

EXAMPLE 4

Sodium 7β-[2-(2-Aminothiazol-4-yl)-2-(Z)-methoxyiminoacetamido]-3-(6-methyl-2-oxo-2H-pyran-4-ylthio)ceph-3-em-4-carboxylate a) Diphenylmethyl 3-(6-Methyl-2-oxo-2H-pyran-4-ylthio) -7β-phenylacetamidoceph-3-em-4-carboxylate and Diphenylmethyl 3-(6-Methyl-2-oxo-2H-pyran-4-ylthio)-7β-phenylacetamidoceph -2-em-4-carboxylate N,N-Diisopropylethylamine (0.3 ml) was added to a stirred solution of diphenylmethyl 3-methylsulphonyloxy-7β-phenylacetamidoceph-3-em-4-carboxylate (0.87 g) and 4-mercapto-6-methyl-2H-pyran-2-one[3] (0.23 g) in dimethylformamide (10 ml). After stirring for 2 hours at room temperature, the mixture was partitioned between ethyl acetate and 1N hydrochloric acid. The organic phase was washed successively with two portions of water, sodium bicarbonate solution, water and brine. The solution was dried over magnesium sulphate and evaporated. The title compounds were isolated as a mixture (712 mg) by column chromatography of the residue using gradient elution (Kieselgel, 2:1 going to 1:2 hexane:ethyl acetate). $v_{max}$ (CHCl$_3$) 3400, 1790 and 1710(br).

b) Diphenylmethyl 3-(6-Methyl-2-oxo-2H-pyran-4-yl-thio) -7β-phenylacetamidoceph-3-em-4-carboxylate 1-oxide A stirred solution of diphenylmethyl 3-(6-methyl-2-oxo-2H-pyran-4-ylthio) -7β-phenylacetamidoceph-3-em-4-carboxylate and diphenylmethyl 3-(6-methyl-2-oxo-2H-pyran-4-ylthio) -7β-phenylacetamidoceph-2-em-4-carboxylate (763 mg) in dichloromethane (10 ml) was cooled in an ice bath, and a solution of m-chloroperbenzoic acid (211 mg of 85%) in dichloromethane (5 ml) was added. The mixture was stirred at 0° for 40 mins. and then washed with sodium bicarbonate solution, sodium metabisulphite solution, water and brine. The solution was dried over magnesium sulphate and evaporated. The title compound (581 mg) was isolated by column chromatography of the residue using gradient elution (Kieselgel 1:1 hexane:ethyl acetate going to neat ethyl acetate). $v_{max}$ (CHCl$_3$) 3390, 1805, 1720 cm$^{-1}$, δ$_H$(CDCl$_3$) 2.14 (3H, s) 3.36 (1H, d, J 18.1Hz), 3.60 (2H, s), 3.75 (1H, d, J 18.2Hz), 4.51 (1H, d, J 4.8Hz), 5.72 (1H, s), 5.95 (1H, s) 6.13 (1H, dd, J 4.8 and 9.7Hz), 6.94 (1H, d, J 9.7Hz), 6.97 (1H, s), 7.2–7.4 (15H, m).

c) Diphenylmethyl 3-(6-Methyl-2-oxo-2H-pyran-4-ylthio) -7β-phenylacetamidoceph-3-em-4-carboxylate A stirred solution of diphenylmethyl 3-(6-methyl-2-oxo-2H-pyran-4-ylthio) -7β-phenylacetamidoceph-3-em-4-carboxylate 1-oxide (581 mg) in dichloromethane (5 ml) was cooled in an ice bath and dimethylacetamide (0.25 ml) was added followed by phosphorus trichloride (0.16 ml). The mixture was stirred at 0° C. for 15 mins. and then partitioned between sodium bicarbonate solution and chloroform. The chloroform layer was washed with water, then brine, dried over magnesium sulphate and evaporated. The title compound (509 mg) was isolated by column chromatography of the residue using gradient elution (Kieselgel, 1:1 hexane: ethyl acetate going to neat ethyl acetate). $v_{max}$(CHCl$_3$) 3400, 1795, 1725, 1710, and 1680 cm$^{-1}$. $\delta_H$(CDCl$_3$) 2.16 (3H, s), 3.33 (1H, d, J 18.1Hz), 3.62 (1H, d, J 17.9Hz), 3.65 (2H, s), 5.03 (1H, d, J 5.1Hz), 5.66 (1H, s) 5.71 (1H, s), 5.94 (1H, dd, J 5.1 and 9.2Hz), 6.96 (1H, s), 6.98 (1H, d, J 9.1Hz), 7.2–7.4 (15H, m). [mass spectrum: +ve ion (3 NOBA, Na+) M Na+ 647].

d) Diphenylmethyl 7β-Amino-3-(6-methyl-2-oxo-2H-pyran-4-ylthio) ceph-3-em-4-carboxylate A stirred solution of diphenylmethyl 3-(6-methyl-2-oxo-2H-pyran-4-ylthio) -7β-phenylacetamidoceph-3-em-4-carboxylate (509 mg) in dichloromethane (6.5 ml) was cooled to $-15°$ to $-20°$ C. N-methylmorpholine (0.18 ml) was added followed by a solution of phosphorus pentachloride in dichloromethane (6.4 ml of solution containing 40 mg ml$^{-1}$). The mixture was stirred at the same temperature for 30 mins. Methanol (1.6 ml) was then added and the mixture stirred at room temperature for 30 mins. Water (2.2 ml) was then added and the mixture vigorously stirred for 45 mins. The dichloromethane was evaporated and the residue partitioned between water and ethyl acetate. The pH of the aqueous phase was adjusted to 6.2 with 1N aqueous ammonia. The organic phase was washed with water, then brine, dried over magnesium sulphate and evaporated. The title compound (332 mg) was isolated by column chromatography of the residue using gradient elution (Kieselgel 1:1 hexane:ethyl acetate going to neat ethyl acetate). $v_{max}$(CHCl$_3$) 1785, 1720, 1705 cm$^{-1}$. $\delta_H$(CDCl$_3$) 1.85 (2H, s), 2.17 (3H, s), 3.30 (1H, d, J 18.1Hz), 3.67 (1H, d, J 18.1Hz), 4.85 (1H, d, J 5.3Hz), 5.05 (1H, d, J 5.4Hz), 5.62 (1H, s), 5.76 (1H, s), 6.99 (1H, s), 7.2–7.4 (10H, m).

e) Diphenylmethyl 3-(6-Methyl-2-oxo-2H-pyran-4-ylthio) -7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (347 mg) and N,N-diisopropylethylamine (0.252 ml) in dimethylformamide (2 ml) was cooled to $-55°$ to $-60°$ C. and methanesulphonyl chloride (0.056 ml) was added. The mixture was stirred at the same temperature for 30 mins., and then a solution of diphenyl 7β-amino-3-(6-methyl-2-oxo-2H-pyran-4-ylthio) ceph-3-em-4-carboxylate (332 mg) in dimethylformamide (4 ml) was added followed by pyridine (0.058 ml). The mixture was then stirred at 0° C. for 1 hour. The mixture was then partitioned between ethyl acetate and sodium bicarbonate solution, the organic phase was washed successively with water, citric acid solution, twice with water and finally with brine. The solution was dried over magnesium sulphate and evaporated. The title compound (228 mg) was isolated by column chromatography of the residue using gradient elution (Kieselgel 1:1 hexane:ethyl acetate going to neat ethyl acetate). $v_{max}$(CHCl$_3$) 3400, 1795, 1720 and 1710 cm$^{-1}$ $\delta_H$(CDCl$_3$) 2.17 (3H, s), 3.32 (1H, d, J 18.2Hz), 3.68 (1H, d, J 18.2Hz), 4.10 (3H, s), 5.16 (1H, d, J 5.0Hz), 5.64 (1H, s), 5.76 (1H, s) 6.02 (1H, dd, J 4.7 and 7.8Hz), 6.74 (1H, s), 6.83 (1H, d, J 7.8Hz), 6.99 (1H, s), 7.2–7.4 (25H, m).

f) Sodium 7β-[2-(2-Aminothiazol-4-yl)-2-(Z)-methoxyiminoacetamido]-3-(6-methyl-2-oxo-2H-pyran-4-ylthio)ceph-3-em-4-carboxylate Diphenylmethyl 3-(6-methyl-2-oxo-2H-pyran-4-ylthio)-7β-[2-(2-tritylaminothiazol-4-yl)-2-(Z)-methoxyiminoacetamido] ceph-3-em-4-carboxylate (228 mg) was dissolved in 98–100% formic acid (5 ml) and 1N hydrochloric acid (0.25 ml) and water (0.25 ml) were added to the stirred solution. The mixture was stirred at room temperature for 30 mins. and then concentrated hydrochloric acid (0.2 ml) was added. After stirring for a further hour the solid was filtered off and the filter cake washed with 90% formic acid. The fitrate was evaporated and toluene evaporated from the residue twice. The residue was triturated with ether and the ether decanted. The residue was stirred with water and toluene and the pH of the aqueous phase adjusted to 6.2 with sodium bicarbonate solution. The aqueous phase was filtered through Celite and evaported. The product was purified by HP20SS chromatography using water with increasing proportions of acetone as eluent. Fractions containing product were combined, evaporated, dissolved in water and freeze dried to give the title compound (67 mg). $v_{max}$ (KBr) 1774, 1675, 1617 cm$^{-1}$. $\delta_H$[(CD$_3$)$_2$SO] 2.17 (3H, s), 3.16 (1H, d, J 16.9Hz), 3.75 (1H, d, J 16.9Hz), 3.84 (3H, s), 5.20 (1H, d, J 5.1Hz), 5.67 (1H, s), 5.69 (1H, dd, J 5.0 and 8.2Hz), 6.18 (1H, s), 6.73 (1H, s), 7.24 (2H, s), 9.74 (1H, d, J 8.3Hz). [mass spectrum: +ve ion (thioglycerol) MH+ 546].

EXAMPLE 5

Sodium 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate a) Diphenylmethyl 3-(2,5-Dihydro-2-oxofuran-4-yl-thiomethyl) -7β-phenylacetamidoceph-3-em-4-carboxylate N,N-Diisopropylethylamine (0.52 ml) was added to a stirred solution of diphenylmethyl 3-chloromethyl-7β-phenylacetamidoceph-3-em-4-carboxylate (1.59 g) and 4-mercapto-2(5H)-furanone (400 mg) in dichloromethane (30 ml). The mixture was stirred at room temperature for 2 hours and then washed successively with aqueous citric acid solution, water, sodium bicarbonate solution, water and brine. The solution was dried over magnesium sulphate and evaporated. The title compound (1.64 g) was isolated by column chromatography of the residue using gradient elution (Kieselgel, 1:1 going to 3:7 hexane:ethyl acetate), m.p. 178°–180° C. from ethyl acetate/hexane (Found: C, 64.89; H, 4.61; N, 4.57; S, 10.30: C$_{33}$H$_{28}$N$_2$O$_6$S$_2$ requires; C, 64.69; H, 4.61; N, 4.57; S, 10.47). $v_{max}$ (CHCl$_3$) 3400, 1780, 1745, and 1680 cm$^{-1}$. $\delta_H$(CDCl$_3$) 3.36 (1H, d, J 18.3Hz), 3.57 (1H, d, J 18.3Hz), 3.62 (1H, d, J 16.2Hz), 3.70 (1H, d, J 16.2Hz), 3.86 (1H, d, J 12.5Hz), 4.01 (1H, d, J 12.5Hz), 4.71 (2H, s), 4.98 (1H, d, J 4.8Hz), 5.64 (1H, s), 5.88 (1H, dd, J 4.8 and 9.0Hz), 6.06 (1H, d, J 9.0Hz), 6.95 (1H, s), 7.2–7.4 (15H, m).

b) Diphenylmethyl 7β-Amino-3-(2,5 dihydro-2-oxofuran-4-ylthiomethyl)ceph-3-em-4-carboxylate A stirred solution of diphenylmethyl 3-(2,5-dihydro-2-oxofuran-4-ylthiomethyl-7β-phenylacetamidoceph-3- em-4-carboxylate (1.95g) in dichloromethane (25ml) was cooled to −15° C. to −20° C., then N-methylmorpholine (0.70 ml) was added followed by a solution of phosphorus pentachloride in dichloromethane (25 ml of a solution containing 40 mg ml$^{-1}$). The solution was stirred at −15° C. to −20° C. for 30 min, then methanol (6.5 ml) was added and the mixture stirred at room temperature for 30 min. Water (8.5 ml) was then added and the mixture vigorously stirred for 30 min. The dichloromethane was then evaporated on a rotary evaporator and the residue partitioned between water and ethyl acetate. The pH of the aqueous phase was adjusted to 6.0 with 1N aqueous ammonia and the organic phase was separated, washed with water, then with brine, dried over magnesium sulphate and evaporated. The title compound (1.28 g) was isolated by column chromatography of the residue using gradient elution (Kieselgel 1:3 hexane:ethyl acetate going to neat ethyl acetate). $\nu_{max}$(CHCl$_3$) 1780 and 1740 cm$^{-1}$. $\delta_H$(CDCl$_3$) 2.45 (2H, br s), 3.45 (1H, d, J 18.1Hz), 3.59 (1H, d, J 18.1Hz), 3.95 (2H, s), 4.69 (2H, s), 4.85 (1H, d, J 5.0Hz), 4.97 (1H, d, J 5.1Hz), 5.63 (1H, s), 6.98 (1H, s), 7.2–7.45 (10H, m). [mass spectrum: +ve ion (3 NOBA, Na$^+$) MNa$^+$ 517].

c) Diphenylmethyl 3-(2,5-Dihydro-2-oxofuran-4-ylthiomethyl)-7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (528 mg) and N,N-diisopropylethylamine (0.383 ml) in dry dimethylformamide (4 ml) was cooled to −55° to −60° C. and methanesulphonyl chloride (0.085 ml) was added. The mixture was stirred at the same temperature for 30 mins, and then diphenylmethyl 7β-amino-3-(2,5-dihydro-2-oxofuran-4-ylthiomethyl)ceph-3-em-4-carboxylate (494 mg), dimethylformamide (2 ml) and pyridine (0.08 ml) were added. The mixture was then stirred at 0° for 90 mins. The mixture was partitioned between ethyl acetate and citric acid solution, and the ethyl acetate phase was washed twice with water, then with saturated sodium bicarbonate solution, then water and finally with brine. The solution was dried over magnesium sulphate and evaporated. The title compound (703 mg) was isolated by column chromatography of the residue using gradient elution (Kieselgel 5:2 going to 3:7 hexane:ethyl acetate). $\nu_{max}$(CHCl$_3$), 3400, 1785, 1745, and 1685cm$^{-1}$. $\delta_H$(CDCl$_3$) 3.42 (1H, d, J 18.3Hz), 3.61 (1H, d, J 18.4Hz), 3.89 (1H, d, J 12.6Hz), 4.04 (1H, d, J 12.6Hz), 4.08 (3H, s), 4.71 (2H, s), 5.08 (1H, d, J 5.0Hz), 5.65 (1H, s), 5.97 (1H, dd, J 4.9 and 8.8Hz), 6.73 (1H, s), 6.84 (1H, d, J 8.7Hz), 6.96 (1H, s), 7.03 (1H, s), 7.2–7.45 (25H, m). [mass spectrum: +ve ion (3 NOBA, Na$^+$) M Na$^+$ 942].

d) Sodium 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate Diphenylmethyl 3-(2,5-dihydro-2-oxofuran-4-ylthiomethyl)-7β-[2-(2-tritylaminothiazol-4-yl)-2-(Z)-methoxyiminoacetamido]ceph-3-em-4-carboxylate (703 mg) was dissolved in 98–100% formic acid (15 ml) and 1N hydrochloric acid (0.765 ml) and water (0.75 ml) were added. The mixture was stirred at room temperature for 30 mins and then concentrated hydrochloric acid (0.6 ml) was added and the mixture stirred for 1 hour. The solid was filtered off and the filter cake washed with 90% formic acid. The combined filtrates were evaporated and toluene was evaporated from the residue twice. The residue was triturated with ether and the ether decanted twice. The residue was stirred with toluene and water and the pH of the aqueous phase was adjusted to 6.2 with saturated sodium bicarbonate solution. The aqueous phase was separated, filtered through Celite and evaporated. The product was purified by chromatrography on HP20SS eluting with water with increasing proportions of acetone. Fractions containing product were combined, evaporated, and the residue dissolved in water and freeze dried to give the title compound (245 mg). $\nu_{max}$ (KBr) 1762, 1736, 1669 and 1603cm$^{-1}$. $\delta_H$[(CD$_3$)$_2$SO] 3.30 (1H, d, J 17.2Hz), 3.51 (1H, d, J 17.2Hz), 3.83 (3H, s), 4.25 (2H, s), 4.94 (2H, s), 5.00 (1H, d, J 4.8Hz), 5.56 (1H, dd, J 4.7 and 8.2Hz), 6.37 (1H, s), 6.73 (1H, s), 7.23 (2H, s), 9.55 (1H, d, J 8.2Hz). [mass spectrum: +ve ion (3 NOBA, Na$^+$) MNa$^+$ 556].

EXAMPLE 6

7β-[2-(2-Aminothiazol-4-yl)-2-(Z)-hydroxyiminoacetamido]-3-(2,5-dihydro-2-oxofuran-4-ylthiomethyl)ceph-3-em-4-carboxylic acid a) Diphenylmethyl 3-(2,5-Dihydro-2-oxofuran-4-yl-thiomethyl)-7β-[2-(2-tritylaminothiazol-4-yl)-2-(Z)-trityloxyiminoacetamido]ceph-3-em-4-carboxylate A stirred solution of sodium 2-(2-tritylaminothiazol-4-yl)-2-(Z)-trityloxyiminoacetate (762 mg) in dimethylformamide (4 ml) was cooled to −55° C. to −60° C. and methanesulphonyl chloride (0.085 ml) was added. The mixture was stirred at the same temperature for 30 mins and then a solution of diphenylmethyl 7β-amino-3-(2,5-dihydro-2-oxofuran-4-ylthiomethyl)ceph-3-em-4-carboxylate (494 mg) in dimethylformamide (4 ml) was added followed by pyridine (0.08 ml). The mixture was then stirred at 0° C. for 90 mins and then partitioned between ethyl acetate and aqueous citric acid solution. The organic phase was washed successively with water, sodium bicarbonate solution, water, and brine. The solution was dried over magnesium sulphate and evaporated. The title compound (744 mg) was isolated by column chromatography of the residue using gradient elution (Kieselgel 2:1 going to 1:1 hexane:ethyl acetate). $\nu_{max}$(CHCl$_3$) 3400, 1785, 1745 and 1685cm$^{-1}$. $\delta H$(CDCl$_3$) 3.23 (1H, d, J 18.2Hz), 3.52 (1H, d, J 18.2Hz), 3.93 (1H, d, J 12.6Hz), 3.99 (1H, d, J 12.5Hz), 4.70 (2H, s), 5.08 (1H, d, J 5.0Hz),5.65 (1H, s), 6.11 (1H, dd, J 5.0 and 8.9Hz), 6.43 (1H, s), 6.75 (1H, s), 6.98 (1H, s), 7.15–7.5 (41H, m). [mass spectrum: +ve ion (thioglycerol) MH$^+$1148].

b) 7β-2-(2-Aminothiazol-4-yl)-2-(Z)-hydroxyiminoacetamido]-3-(2,5-dihydro-2-oxofuran-4-ylthio methyl)ceph-3-em-4-carboxylic Acid Diphenylmethyl 3-(2,5-dihydro-2-oxofuran-4-ylthiomethyl)-7β-[2-(2-tritylaminothiazol-4-yl)-2-(Z)-trityloxyiminoacetamido]ceph-3-em-4-carboxylate (744 mg) was dissolved in 98–100% formic acid (13 ml) and 1N hydrochloric acid (0.65 ml) and water (0.65 ml) were added. The mixture was stirred at room temperature for 30 mins and then concentrated hydrochloric acid (0.52 ml) was added. After stirring for a further hour the solvents were removed on a rotary evaporator.

A mixture of toluene and tetrahydrofuran was evaporated from the residue twice, and the residue triturated with ether. The solid was filtered off, and washed with ether. The solid was suspended in water and the pH adjusted to 2.6 with 0.1N sodium hydroxide, the mixture was stirred for a further 30 mins, occasionally adjusting the pH to 2.6. The solid was then filtered off, washed with cold water and dried under vacuum to give the title compound (128 mg) as an off-white solid. $v_{max}$(KBr) 1773, 1735, 1670, and 1629cm$^{-1}$. $\delta_H$[(CD$_3$)$_2$SO] 3.49 (1H, d, J 18.0Hz), 3.72 (1H, d, J 18.1Hz), 4.10 (1H, d, J 13.2Hz), 4.18 (1H, d, J 13.2Hz), 4.97 (2H, s), 5.18 (1H, d, J 4.8Hz), 5.79 (1H, dd, J 4.8 and 8.0Hz), 6.11 (1H, s), 6.67 (1H, s), 9.51 (1H, d, J 8.1Hz), 11.40 (1H, s). [mass spectrum: +ve ion (thioglycerol) MH+ 498].

EXAMPLE 7

Sodium 7β-[2-(2-Aminothiazol-4-yl)-2-(Z)-methoxyiminoacetamido]-3-(2,5-dihydro-2-oxofuran-3-ylmethylthio)ceph-3-em-4-carboxylate (a) Diphenylmethyl 3-(2,5-Dihydro-2-oxofuran-3-yl-methylthio)-7β-phenylacetamidoceph-3-em-4-carboxylate N,N-Diisopropylethylamine (0.40 ml) was added to a mixture of diphenylmethyl 3-mercapto-7β-phenylacetamidoceph-3-em-4-carboxylate (1.20 g) and 3-bromomethyl-2(5H)-furanone[4] (0.41g) in tetrahydrofuran (15 ml). The mixture was stirred at room temperature for 2 hours before removing the solvent by evaporation in vacuo. The residue was partitioned between ethyl acetate/water. The organic phase was washed with water, and brine, before drying over magnesium sulphate. Evaporation of solvent was followed by chromatography using gradient elution (Keiselgel, 2% acetone:dichloromethane going to 4% acetone:dichloromethane). Evaporation followed by crystallization from ethyl acetate/hexane gave the title compound (0.83g). m.p. 171° C. from ethyl acetate/hexane (Found: C, 64.55; H, 4.48; N, 4.94; S, 10.27; C$_{33}$H$_{28}$N$_2$O$_6$S$_2$ requires; C, 64.69; H, 4.60; N, 4.57; S, 10.47)]$v_{max}$ (CH$_2$Cl$_2$) 3410, 1790, and 1745cmhu −1; $\delta_H$ (CDCl$_3$) 3.37–3.56 (4H, m), 3.62 (1H, d, J 16.1Hz), 3.69 (1H, d, J 16.1Hz), 4.71 (2H, bs), 4.97 (1H, d, J 4.7Hz), 5.76 (1H, dd, J 8.9Hz and 4.7Hz), 6.24 (1H, d, J 8.9Hz), 6.92 (1H, s), 7.15 (1H, t, J 1.4Hz), 7.26–7.44 (15H, m).

(b) Diphenylmethyl 7β-Amino-3-(2,5-dihydro-2-oxofuran-3-ylmethylthio)-ceph-3-em-4-carboxylate Diphenylmethyl 3-(2,5-dihydro-2-oxofuran-3-yl-methylthio)-7β-phenylacetamidoceph-3-em-4-carboxylate (0.83g) was dissolved in dichloromethane (11 ml) and treated with N-methylmorpholine (298μl). The atmosphere was purged with argon and the mixture cooled to −30° C. A solution of phosphorus pentachloride in dichloromethane (10.6 ml of 40 mg ml$^{-1}$ solution) was added and the reaction stirred at approximately −20° C. for 30 min. Methanol (2.7 ml) was added and the reaction allowed to warm to room temperature. Water (3.6 ml) was then added and the mixture stirred vigorously for 45 min. Dichloromethane was removed using a rotary evaporator and the residue partitioned between ethyl acetate and water. The pH of the solution was adjusted to 6.0 with 1.0M aqueous ammonia before separating the organic phase, washing with water and brine, and finally drying over magnesium sulphate. Evaporation of solvent gave a residue which was purified by chromatography on silica gel (Keiselgel, 7:3 ethyl acetate:hexane) to give the title compound (600 mg). $v_{max}$ (CH$_2$Cl$_2$) 1780 and 1760cmhu −1; $\delta_H$(CDCl$_3$) 2.04 (2H, bs) 3.44–3.73 (4H, m), 4.70 (2H, s), 4.77 (1H, d, J 5.0Hz), 4.96 (1H, d, J 4.9Hz), 6.96 (1H, s) 7.11 (1H, s), 7.27–7.46 (10H, m). [mass spectrum: +ve ion (Thioglycerol) MH+ 495].

(c) Diphenylmethyl 3-(2,5-Dihydro-2-oxofuran-3-yl-methylthio)-7β-[2-(2-tritylaminothiazol-4-yl)-2-(Z)-methoxyiminoacetamido]ceph-3-em-4-carboxylate A stirred solution of 2-(2-Tritylaminothiazol-4-yl)-2-(Z)-methoxyiminoacetic acid hydrochloride (287 mg) and diisopropylethylamine (0.208 ml) in dry dimethylformamide (5 ml) was cooled to −50° C. under an inert atmosphere. Treatment with methanesulfonyl chloride (0.047 ml) was followed by stirring at −50° C. for 45 min. Pyridine (0.048 ml) and a solution of diphenylmethyl-7β-amino-3-(2,5-dihydro-2-oxofuran-3-ylmethylthio)ceph-3-em-4-carboxylate (298 mg) in dimethylformamide (3 ml) were then added and the reaction allowed to warm to 0° C. The reaction was stirred at 0° C. for 90 min. before pouring into ethyl acetate/water. The ethyl acetate was separated and washed three times with water, saturated sodium bicarbonate solution, and brine before drying over magnesium sulphate. Evaporation of solvent and chromatography of the residue on silica gel(Keiselgel 7:3 ethyl acetate:hexane) gave the title compound (364 mg). $v_{max}$(CH$_2$Cl$_2$) 3400, 1780, and 1760cm$^{-1}$; $\delta_H$(CDCl$_3$) 3.50 (1H, d, J 17.4Hz), 3.53 (2H, s), 3.67 (1H, d, J 17.4Hz), 4.08 (3H, s), 4.72 (2H, s), 5.08 (1H, d, J 4.7Hz), 5.88 (1H, dd, J 8.6Hz, 4.7Hz), 6.76 (1H, s), 6.83 (1H, d, J 8.8Hz), 6.90 (1H, s), 6.95 (1H, s), 7.16–7.46 (26H, m). [mass spectrum: +ve ion (3NOBA, Na+) MNa+ 942].

(d) Sodium 7β-[2-(2-Aminothiazol-4-yl)-2-(Z)-methoxyiminoacetamido]-3-(2,5-dihydro-2-oxofuran-3-ylmethylthio)ceph-3-em-4-carboxylate.

Diphenylmethyl 3-(2,5-dihydro-2-oxofuran-3-ylmethylthio)-7β-[2-(2-tritylaminothiazol-4-yl)-2-(Z)-methoxyiminoacetamido]ceph-3-em-4-carboxylate (364 mg) was dissolved in 98–100% formic acid (4.0 ml) and treated with 1.0M hydrochloric acid (0.40 ml). The reaction was stirred for 30 min. at room temperature. One drop of concentrated hydrochloric acid was then added and stirring continued for 60 min. Any solid matter was removed by filtration at this stage and the solid washed with a small amount of 90% formic acid. The filtrate was evaporated to dryness followed by evaporation of toluene from the residue (three times). The residue was dissolved in ethyl acetate/water and the pH adjusted to 6.2 with saturated sodium bicarbonate solution. The aqueous phase was separated, evaporated to low volume and chromatographed on HP20SS eluting with aqueous solutions containing an increasing proportion of tetrahydrofuran. The product containing fractions were combined, evaporated to low volume and freeze dried to give the title compound as a white solid (163 mg). $v_{max}$ (KBr disc) 1749, 1664, 1611, and 1532cm$^{-1}$; $\delta_H$(D$_2$O) 3.47 (1H, d, J 17.3Hz), 3.51 (1H, d, J 14.9Hz), 3.62 (1H, d, J=14.7Hz), 3.77 (1H, d, J 17.4Hz), 3.95 (3H, s), 4.91 (2H, s), 5.18 (1H, d, J 4.5Hz), 5.74 (1H, d, J 4.6Hz), 7.00 (1H, s), 7.58 (1H, s). [mass spectrum: +ve ion (thioglycerol) MH+ 534].

EXAMPLE 8

7β-[2-(2-Aminothiazol-4-yl)-2-(Z)-hydroxyiminoacetamido]-3-(2,5-dihydro-2-oxofuran-3-ylmethylthio)ceph-3-em-4-carboxylic acid (a) Diphenylmethyl 3-(2,5-Dihydro-2-oxofuran-3-ylmethylthio)-7β-[2-(2-tritylaminothiazol-4-yl)-2-(Z)trityloxyiminoacetamido]-ceph-3-em-4-carboxylate A stirred solution of sodium 2-(2-tritylaminothiazol-4-yl)-2-trityloxyiminoacetate (420 mg) in dimethylformamide (5 ml) was cooled to −50° C. whilst under an inert atmosphere. Methanesulphonyl chloride (0.047 ml) was added and the reaction stirred at −50° C. for 30 min. Pyridine (0.049 ml) was added followed by a solution of diphenylmethyl 7β-amino-3-(2,5-dihydro-2-oxofuran-3-ylmethylthio)ceph-3-em-4-carboxylate (300 mg) in dimethylformamide (3 ml) and the reaction was allowed to warm to 0° C. After stirring at 0° C. for 90 min the mixture was partitioned between ethyl acetate and water. The organic phase was separated and washed twice with water followed by saturated sodium bicarbonate and finally brine. After drying over magnesium sulphate and evaporation of solvent the residue was purified by chromatography on silica gel (Keiselgel, 2:3 ethyl acetate:hexane rising to 7:3 ethyl acetate:hexane). The title compound was isolated as a foam (422 mg). $\nu_{max}$ (CH$_2$Cl$_2$) 3380, 1785, 1760 and 1725cm$^{-1}$; $\delta_H$(CDCl$_3$) 3.25 (1H, d, J 17.3Hz), 3.49–3.56 (3H, m), 4.68 (2H, s), 5.08 (1H, d, J 4.9Hz), 6.00 (1H, dd, J 8.8Hz, 4.9Hz), 6.44 (1H, s), 6.74 (1H, bs), 6.98 (1H, s), 7.12 (1H, s), 7.16–7.49 (41H, m). [mass spectrum: +ve ion (3NOBA, Na+) MNa+ 1170].

(b) 7β-[2-(2-Aminothiazol-4-yl)-2-(Z)-hydroxyiminoacetamido]-3-(2,5-dihydro-2-oxofuran-3-ylmethylthio)ceph-3-em-4-carboxylic acid Diphenylmethyl 3-(2,5-dihydro-2-oxofuran-3-ylmethylthio)-7β-[2-(2-tritylaminothiazol-4-yl)-2-(Z)-trityloxyiminoacetamido]ceph-3-em-4-carboxylate (422 mg) was completely dissolved in 98–100% formic acid (3.7 ml) and then treated with 1.0M hydrochloric acid (370 μl). After stirring at room temperature for 45 mins. a drop of concentrated hydrochloric acid was added and stirring continued for 1 hour. The solvent was removed and then toluene was twice evaporated from the residue. The residue was triturated with ether and the resulting solid collected and washed with ether. Suspension of the solid in water was followed by adjustment of the pH to 2.6 with 0.1M sodium hydroxide. Care was taken to allow time for pH equilibration between additions of alkali. The solid was filtered, washed with cold water and dried in vacuo to give the title compound as an amorphous solid (87 mg). $\nu_{max}$ (KBr disc) 1775 and 1750cm$^{-1}$; $\delta_H$[(CD$_3$)$_2$SO] 3.57–3.84 (4H, m), 4.85 (2H, s), 5.16 (1H, d, J 4.7Hz), 5.73 (1H, dd, J 8.3Hz, 4.7Hz), 6.67 (1H, s), 7.16 (2H, bs), 7.57 (1H, s), 9.48 (1H, d, J 8.3Hz), 11.30 (1H, bs). [mass spectrum: +ve ion (thioglycerol) MH+ 498].

EXAMPLE 9

Sodium 7β-2-(2-Aminothiazol-4-yl)-2-(Z)-methoxyiminoacetamido]-3-(2-oxotetrahydrofuran-3-ylthio)-ceph-3-em-4-carboxylate.

(a) Diphenylmethyl 3-(2-oxotetrahydrofuran-3-ylthio)-7β-phenylacetamidoceph-3-em-4-carboxylate.

Diphenylmethyl-3-methoxy-7β-phenylacetamidoceph-3-em-4-carboxylate (2.0g) was dissolved in dimethylformamide (40 ml). The solution was cooled to −5° C. and then treated with sodium hydrosulphide (20 g), benzyltrimethylammonium chloride (1.8 g) and finally 1,8-diazabicyclo[5.4.0]undec-7-ene (1.5 ml). The reaction was stirred for 30 min. Diluted with ethyl acetate and washed sequentially with dilute citric acid, water (three times) and brine. After drying over anhydrous magnesium sulphate the solvents were removed by evaporation in vacuo to give crude diphenylmethyl-3-mercapto-7β-phenylacetamidoceph-3-em-4-carboxylate. This was dissolved in dry tetrahydrofuran (15 ml) and treated with α-bromobutyrolactone (640 mg) followed by diisopropylethylamine (640 μl). The reaction was stirred at room temperature for 45 min. The solvent was removed by evaporation in vacuo and the residue partitioned between ethyl acetate and water. After separation the organic phase was washed with saturated sodium chloride before drying over anhydrous magnesium sulphate. The crude material was purified by chromatography on silica gel (Keiselgel) using gradient elution (1:50 acetone:dichloromethane rising to 1:25 acetone: dichloromethane). The material was crystalized from chloroform/ethyl acetate to give the title compound as a mixture of diastereomers (836 mg), m.p. 198°–199° C. $\nu_{max}$(CH$_2$Cl$_2$) 3400, 1780, 1730, and 1685cm$^{-1}$; $\delta_H$(CDCl$_3$) 1.89–2.05 (1H, m), 2.24–2.57 (1H, m), 3.58 (1H, d, J17.2Hz) superimposed on 3.58–3.76 (2H, m), 3.87 (1H, d, J17.2Hz), 4.13–4.29 (2H, m) 4.98–5.02 (1H, m), 5.83 (1H, dd, J9.2Hz, 4.1Hz), 6.29–6.37 (1H, m), 6.80 and 6.68 (1H, s+s), and 7.25–7.43 (15H, m). [mass spectrum:+ve ion (3NOBA/Na+)MNa+ 623].

(b) Diphenylmethyl 7β-Amino-3-(2-oxotetrahydrofuran-3-ylthio)ceph-3-em-4-carboxylate.

Diphenylmethyl 3-(2-oxotetrahydrofuran-3-ylthio)-7β-phenylacetamidoceph-3-em-4-carboxylate (733 mg) was suspended in dry dichloromethane (10 ml) under an inert atmosphere. The reaction was cooled to −20° C. and treated with N-methylmorpholine (269 μl) followed by a solution of phosphorus pentachloride in dichloromethane (9.5 ml of 40 mgml$^{-1}$ solution). The now homogeneous solution was stirred at −20° C. for 30 min. Treated with methanol (2.44 ml) and then continued stirring whilst allowing to warm to room temperature. After 30 min. water (3.3 ml) was added and the solution vigorously stirred for a final 30 min. The organic solvent was removed by evaporation in vacuo. The resulting solid was removed from the aqueous phase by filtration and was washed with water and then ether. Drying the solid over phosphorus pentoxide in vacuo gave the crude title compound in the form of its hydrochloride (621 mg). (c) Diphenylmethyl 3-(2-Oxotetrahydrofuran-3-ylthio)-7β-[2-(2-trylaminothiazol-4-yl)-2-(Z)-methoxyiminoacetamido]ceph-3-em-4-carboxylate.

A stirred solution of 2-(2-Tritylaminothiazol-4-yl)-2-(Z)-methoxyiminoacetic acid hydrochloride (570 mg) in dimethylformamide (5 ml) was cooled to −50° C. under an inert atmosphere. The solution was treated with diisopropylethylamine (414 μl) followed by methanesulphonyl chloride (92 μl). The reaction was stirred at −50° C. for 45 min. before treating with pyridine (96 μl) followed by a solution of diphenylmethyl 7β-amino-3-(2-oxotetrahydrofuran-3-ylthio)ceph-3-em-4-carboxylate (621 mg) in dimethylformamide (2 ml). The reaction was allowed to warm to 0° C. and then stirred for 1 h. After pouring into ethylacetate/water the organic phase was washed with a further portion of water followed by saturated sodium bicarbonate solution and finally brine. Drying over anhydrous magnesium sulphate followed by removal of solvent gave a residue which was purified by chromatography on silica gel (Keiselgel) using gradient elution (1:1 ethyl acetate:hexane rising to 7:3 ethyl acetate:hexane). The title compound was finally isolated as a mixture diastereomers (417 mg). $v_{max}(CH_2Cl_2)$ 3400, 1790, 1735, 1690, and 1520cm$^{-1}$, $\delta_H(CDCl_3)$ 1.94–2.07 (1H, m), 2.35–2.69 (1H,m), 3.62–3.87 (3H, m), 4.08 (3H, s) superimposed on 4.00–4.27 (2H, m), 5.10 and 5.13 (1H, d, J3.6Hz), 5.90–5.97 (1H, m), 6.75 (1H, s), 6.83 (1H, d, J9Hz), 6.92 and 6.99 (1H, s+s), 7.01 (1H, s), and 7.26–7.42 (25H, m). [mass spectrum:+ve ion (3NOBA/Na+) M-H+Na]+ 929].

(d) Sodium 7β-[2-(2-Aminothiazol-4-yl)-2-(Z)-methoxyiminoacetamido]-3-(2-oxotetrahydrofuran-3-ylthio)-ceph-3-em-4-carboxylate.

Diphenylmethyl 3-(2-oxotetrahydrofuran-3-ylthio)-7β-[2-(2-tritylaminothiazol-4-yl)-2-(Z)-methoxyiminoacetamido]ceph-3-em-4-carboxylate (417 mg) was dissolved in 98–100% formic acid (4.5 ml) and then treated with 1.0 m hydrochloric acid (460 μl). After stirring for 30 min. two drops of concentrated hydrochloric acid were added and stirring continued for 1 h. The solid was removed by filtration and then washed with a small amount of 90% formic acid. The filtrate was evaporated to dryness and toluene evaporated from the residue. After dissolution of the residue in ethyl acetate/water the pH was adjusted to 6.5 with saturated sodium bicarbonate solution. The aqueous phase was separated, evaporated to low volume and then purified by chromatography on HP20SS resin eluting with water containing an increasing proportion of tetrahydrofuran. The product was then freeze dried giving the title compound as a mixture of diastereoisomers (144 mg). $v_{max}$(KBr disc) 1762, 1665, 1610, and 1530cm$^{-1}$; $\delta_H(D_2O)$ 2.19–2.31 (1H, m), 2.64–2.72 (1H, m), 3.48 and 3.55 (1H, d+d, J13.1Hz), 3.82–3.89 (1H, m) 3.96 (3H, s) superimposed on 3.94–4.16 (1H, m), 4.34–4.53 (2H, m), 5.23–5.26 (1H, m) 5.78–5.80 (1H, m), and 6.98 (1H, s). [mass spectrum:+ve ion (thioglycerol) MH+ 522].

EXAMPLE 10

Pivaloyloxymethyl-7β-[2-(2-aminothiazol-4-yl)-2-(Z)-methoxyiminoaoetamido]-3-(2.5-dihydro-2-oxofuran-3-ylmethylthio)ceph-3-em-4-carboxylate.

Pivaloyloxymethyl bromide (70 mg) was dissolved in acetone (3 ml) in a vessel from which light had been excluded. The solution was treated with sodium iodide (107 mg) and the reaction stirred at RT for 15 min. The reaction mixture was then filtered through Keiselguhr and the filtrate evaported to dryness. The residue was triturated with toluene and the resulting mixture filtered into a solution of sodium 7β-[2-(2-aminothiazol-4-yl)-(Z)-methoxyiminoacetamido]-3-(2,5-dihydro-2-oxofuran-3-ylmethylthio)ceph-3-em-4-carboxylate (153 mg) in 1-methyl-2-pyrollidinone (3 ml). The reaction was stirred at RT for 30 min. Toluene was removed by evaporation in vacuo and the remaining solution partitioned between ethyl acetate and water. The organic phase was washed with water (five times) and brine before drying over anhydrous magnesium sulphate. Chromatography on silica gel (Keiselgel; 7:3 ethyl acetate:hexane rising to neat ethyl acetate) gave the pure title compound as an amorphous solid (130 mg). $v_{max}(CH_2Cl_2)$ 3470, 2960, 1780, 1750, and 1680cm$^{-1}$; $\delta_H(CDCl_3)$ 1.23 (9H, s), 3.56–3.75 (2H, m) 4.07 (2H, s), 4.86 (2H, s), 5.12 (1H, d, J4.9Hz), 5.35 (2H, bs, ex.in $D_2O$), 5.86 (1H, d, J5.5Hz) 5.91 (1H, d, J5.6Hz), 5.98 (1H, dd, J8.9Hz, 4.8Hz), 6.87 (1H, s), 7.45 (1H, s), and 7.54 (1H, d, J8.8Hz). [mass spectrum:+ve ion (3NOBA/Na+) MH+ 626 MNa+ 648].

EXAMPLE 11

Pivaloyloxymethyl 7β-[2-(2-Aminothiazol-4-yl)-2-(Z)-methoxyiminoacetamido]-3-(2-oxotetrahydrofuran-3-yl thio)ceph-3-em-4-carboxylate.

Sodium 7β-[2-(2-aminothiazol-4-yl)-(Z)-methoxyiminoacetamido]-3-(2-oxotetrahydrofuran-3-ylthio)-ceph-3-em-4-carboxylate (119 mg) was reacted to give the title compound (83 mg) in the manner described in Example 10 $v_{max}(CH_2Cl_2)$ 1785, 1750 and 1730cm$^{-1}$; $\delta_H(CDCl_3)$ 1.24 (9H, s), 2.15–2.32 (1H, m), 2.62–2.82 (1H, m), 3.72–4.12 (6H, m), 4.30–4.52 (2H, m), 5.10–5.18 (1H, m), 5.40 (2H, bs), 5.82 (3H, m), 6.97 (1H, s), and 7.27 (1H, m). [mass spectrum:+ve ion (3NOBA/Ma+) MNa+ 636].

EXAMPLE 12

7β-[2-(2-Aminothiazol-4-yl)-2-(Z)-hydroxyiminoacetamido]-3-(2,5-dihydro-2-oxofuran-4-ylmethylthio)ceph-3-em-4-carboxylic acid (a) Diphenylmethyl 3-(2,5-Dihydro-2-oxofuran-4-ylmethylthio)-7β-[2-(2-tritylaminothiazol-4-yl)-2-(Z)-trityloxyiminoacetamido]ceph-3-em-4-carboxylate A stirred solution of sodium 2-(2-tritylaminothiazol-4-yl)-2-(Z)-trityloxyiminoacetate (715 mg) in dimethylformamide (4 ml) was cooled to −55° C. to −60° C. and methanesulphonyl chloride (0.08 ml) was added. The mixture was stirred at the same temperature for 0.5 h. and then a solution of diphenylmethyl 7β-amino-3-(2,5-dihydro-2-oxofuran-4-ylmethylthioceph-3-em-4-carboxylate (462 mg) in dimethylformamide (4 ml) was added followed by pyridine (0.085 ml) and the mixture was warmed to 0° C. After stirring at 0° C. for 1.5 h. the mixture was partitioned between ethyl acetate and citric acid solution. The organic phase was then washed successively with water, sodium bicarbonate solution, water and brine. The solution was dried over magnesium sulphate and evaporated. The product (784 mg) was isolated by column chromatography of the residue using gradient elution (Kieselgel, 1:1 hexane:ethyl acetate going to neat ethyl acetate). $v_{max}(CHCl_3)$ 3400, 1785, 1750, 1685cm$^{-1}$ $\delta(CDCl_3)$ 3.24 (1H, d, J 17.2Hz), 3.45 (1H, d, J 17.1Hz), 3.50 (1H, d, J 14.8Hz), 3.63 (1H, d, J 15.1Hz), 4.61 (2H, s), 5.07 (H, d, J 4.9Hz), 5.87 (1H, s), 6.03 (1H, br s), 6.44 (1H, s), 6.75 (1H, s), 6.99 (1H, s), 7.1–7.5 (41H, m).

(b) 7β-2-(2-Aminothiazol-4-yl)-2-(Z)-hydroxyiminoacetamido]-3-(2,5-dihydro-2-oxofuran-4-ylmethylthio)ceph-3-em-4-carboxylic Acid Diphenylmethyl 3-(2,5-dihydro-2-oxofuran-4-ylmethylthio)-7β-[2-(2-tritylaminothiazol-4-yl)-2-(Z)-trityloxyiminoacetamido]ceph-3-em-4-carboxylate (723 mg) was dissolved in 100% formic acid (13 ml) and 1N hydrochloric acid (0.63 ml) and water (0.63 ml) were added. The mixture was stirred at room temperature for 0.5 hr. and then concentrated hydrochloric acid (0.5 ml) was added. The mixture was stirred at room temperature for a further 0.5h. and then the solid was filtered off and washed with 90% formic acid. The combined filtrates were evaporated and toluene was evaporated from the residue twice. The residue was triturated with three portions of ether which were decanted from the solid. The residue was stirred with water and the pH adjusted to 2.6 with 0.01N sodium hydroxide. The product was filtered off, washed with water and dried under vacuum to give 54 mg of solid. The filtrates were evaporated to ca 5 ml and the solid so formed (79 mg) was isolated as before. $v_{max}$(KBr) 1774, 1741, 1665(s), and 1630cm$^{-1}$δ[(CD$_3$)$_2$SO] 3.72 (2H, s), 3.91 (1H, d, J 15.9Hz), 4.00 (1H, d, J 16.0Hz), 4.86 (1H, d, J 17.6Hz), 4.95 (1H, d, J 17.9Hz), 5.19 (1H, d, J 4.8Hz), 5.76 (1H, dd, J 4.7 and 8.2Hz), 6.07 (1H, s), 6.66 (1H, s), 7.15 (2H, s), 9.52 (1H, d, J 8.2Hz), 11.32 (1H, s). [Mass spectrum: +ve ion (thioglycerol) MH$^+$ 498].

EXAMPLE 13

Sodium 7β-[2-(2-Aminothiazol-4-yl)-2-(Z)-methoxyiminoacetamido]-3-(3-chloro-2,5-dihydro-2-oxofuran-4-ylthiomethyl)ceph-3-em-4-carboxylate (a) Diphenylmethyl 3-(3-Chloro-2,5-dihydro-2-oxofuran-4-ylthiomethyl)-7β-phenylacetamidoceph-3-em-4-carboxylate Phosphorus pentasulphide (0.44 g) was added to a stirred mixture of 3-chlorotetronic acid$^5$ (1.345 g) and dioxan (30 ml). The mixture was heated at 80° for 3 hours and then at 100° for 21 hours. The dioxan was then evaporated under vacuum and the residue partitioned between ethyl acetate and water. The organic phase was washed with brine, dried over magnesium sulphate and evaporated. The resultant 3-chloro-2,5-dihydro-4-mercapto-2-oxofuran was partially purified by column chromatography (Kieselgel, 10% acetic acid in ethyl acetate as eluent) to give 534 mg of impure thiol. This thiol and diphenylmethyl 3-chloromethyl-7β-phenylacetamidoceph-3-em-4-carboxylate (1.065g) were stirred in dichloromethane (20 ml) and N,N-diisopropylethylamine (0.34 ml) was added. The mixture was stirred at room temperature for 2½ hours and then washed successively with citric acid solution, water, sodium bicarbonate solution, water and brine. The solution was dried over magnesium sulphate and evaporated. The product was isolated by column chromatography of the residue using gradient elution (Kieselgel, 3:2 hexane:ethyl acetate going to neat ethyl acetate). $v_{max}$(CHCl$_3$) 3400, 1775, 1725, 1680cm$^{-1}$; δ(CDCl$_3$) 3.38 (1H, d, J 18.3Hz), 3.55 (1H, d, J 18.3Hz), 3.60 (1H, d, J 16.1Hz), 3.69 (1H, d, J 16.1Hz), 3.95 (1H, d, J 12.8Hz), 4.06 (1H, d, J 12.9Hz), 4.55 (1H, d, J 16.3Hz), 4.64 (1H, d, J 16.2Hz), 4.99 (1H, d, J 5.0Hz), 5.87 (1H, dd, J 4.9 and 9.0Hz), 6.20 (1H, d, J 8.9Hz), 7.2–7.45 (16H, m).

(b) Diphenylmethyl 7β-Amino-3-(3-chloro-2,5-dihydro-2-oxofuran-4-ylthiomethyl)ceph-3-em-4-carboxylate A stirred solution of diphenylmethyl 3-(3-chloro-2,5-dihydro-2-oxofuran-4-ylthiomethyl)-7β-phenylacetamidoceph-3-em-4-carboxylate (770 mg) in dichloromethane (10 ml) was cooled to −15° C. to −20° C., then N-methylmorpholine (0.263 ml) was added followed by a solution of phosphorus pentachloride in dichloromethane (9.3 ml of a solution containing 40 mg ml$^{-1}$). The mixture was stirred at the same temperature for 0.5 h. Methanol (2.4 ml) was then added and the mixture stirred at room temperature for 0.5 h. Water (3.2 ml) was then added and the mixture vigorously stirred for a further 0.5 h. The dichloromethane was removed on a rotary evaporator and the residue partitioned between ethyl acetate and water. The pH of the aqueous phase was adjusted to 6.2 with 1N aqueous ammonia. The organic phase was separated, washed with water and brine, dried over magnesium sulphate and evaporated. The product (447 mg) was isolated by column chromatography using gradient elution (Kieselgel, 1:1 hexane:ethyl acetate going to neat ethyl acetate). $v_{max}$(CHCl$_3$) 1775, 1625cm$^{-1}$; δH(CDCl$_3$), 1.77 (2H, br s), 3.43 (1H, d, J 18.16Hz), 3.63 (1H, d, J 18.12Hz), 3.94 (1H, d, J 12.98Hz), 4.05 (1H, d, J 12.93Hz), 4.51 (1H, d, J 16.20Hz), 4.60 (1H, d, J 16.17Hz), 4.81 (1H, d, J 5.11Hz), 4.97 (1H, d, J 5.11Hz), 6.98 (1H, s), 7.25–7.45 (10H, m).

(c) Diphenylmethyl 3-(3-Chloro-2,5-dihydro-2-oxofuran-4-ylthiomethyl)-7β-[2-(2-tritylaminothiazol-4-yl)-2-(Z)-methoxyiminoaoetamido]ceph-3-em-4-carboxylate A stirred solution of 2-(2-tritylaminothiazol-4-yl)-2-(Z)-methoxyiminoacetic acid hydrochloride (445 mg) in dimethylformamide (4 ml) was cooled to −55° C. to −60° C. and N,N-diisopropylethylamine (0.322 ml) was added followed by methanesulphonyl chloride (0.071 ml). The mixture was stirred at the same temperature for 0.5 h and then a solution of diphenylmethyl 7β-amino-3-(3-chloro-2,5-dihydro-2-oxofuran-4-ylthiomethyl)ceph-3-em-4-carboxylate (445 mg) in dimethylformamide (4 ml) was added followed by pyridine (0.067 ml). The mixture was then stirred at 0° for 1.5 h. The mixture was then partitioned between ethyl acetate and citric acid solution. The organic phase was washed successively with water, sodium bicarbonate solution, water and brine. The solution was dried over magnesium sulphate and evaporated. The product (326 mg) was isolated by repeated column chromatography of the product using gradient elution (Kieselgel 1:1 going to 3:7 hexane:ethyl acetate). $v_{max}$(CHCl$_3$) 3400, 1770, 1725, 1685cm$^{-1}$; δ(CDCl$_3$) 3.45 (1H, d, J 18.23Hz), 3.62 (1H, d, J 18.24Hz), 4.04 (2H, s), 4.08 (3H, s), 4.55 (1H, d, J 16.15Hz), 4.63 (1H, d, J 16.16Hz), 5.09 (1H, d, J 4.97Hz), 5.97 (1H, dd, J 4.93 and 8.80Hz), 6.74 (1H, s), 6.83 (1H, d, J 8.79Hz), 6.96 (1H, s), 7.00 (1H, s), 7.25–7.4 (15H, m).

(d) Sodium
7β-[2-(2-Aminothiazol-4-yl)-2-(Z)-methoxyiminoacetamido]-3-(3-chloro-2,5-dihydro-2-oxofuran-4-ylthiomethyl)ceph-3-em-4-carboxylate Hydrochloric acid (0.34 ml of 1N) and water (0.34 ml) were added to a stirred solution of diphenylmethyl 3-(3-chloro-2,5-dihydro-2-oxofuran-4-ylthiomethyl)-7β-[2-(2-tritylaminothiazol-4-yl)-2-(Z)-methoxyiminoacetamido]ceph-3-em-4-carboxylate (326 mg) in 100% formic acid. The mixture was stirred at room temperature for 1¼ h and then filtered. The filter cake was washed with 90% formic acid and the combined filtrates evaporated. A 1:1 mixture of tetrahydrofuran and toluene was evaporated from the residue twice, and then the residue was triturated with ether and the solid filtered off and washed with ether. The solid was suspended in water and the pH adjusted tp 6.2 with sodium bicarbonate solution. The solution was filtered through Celite and evaporated to ca 15 ml. The product was isolated by HP20SS chromatography (water with increasing proportions of acetone as eluent). Fractions containing product were evaporated almost to dryness and the residue dissolved in ca 15 ml of water and freeze-dried to give 110 mg of product. $\nu_{max}$(KBr) 1757, 1670 and 1604cm$^{-1}$; $\delta$[(CD$_3$)$_2$SO] 3.34 (1H, d, J 17.21Hz), 3.57 (1H, d, J 17.21Hz), 3.84 (3H, s), 4.23 (2H, s), 5.05 (1H, d, J 4.80Hz), 5.23 (1H, d, J 17.01Hz), 5.44 (1H, d, J 17.01Hz), 5.58 (1H, dd, J4.78 and 8.19), 6.73 (1H. s), 7.21 (2H, s), 9.52 (1H, d, J 8.21Hz).

EXAMPLE 14
Sodium
7β-[2-(2-Aminothiazol-4-yl)-2-(Z)-methoxyiminoacetamido]-3-(6-methyl-2-oxo-2H-pyran-4-ylthiomethyl)ceph-3-em-4-carboxylate

(a) Diphenylmethyl
3-(6-methyl-2-oxo-2H-pyran-4-ylthiomethyl)-7β-phenylacetamidoceph-3-em-4-carboxylate N,N-Diisopropylethylamine (0.43 ml) was added to a stirred solution of diphenylmethyl 3-chloromethyl-7β-phenylacetamidoceph-3-em-4-carboxylate (1.33g) and 4-mercapto-6-methyl-2H-pyran-2-one[3] (384 mg) in dichloromethane (25 ml). The mixture was stirred at room temperature for 1 h and then washed successively with citric acid solution, water, sodium bicarbonate solution, water and brine. The solution was dried over magnesium sulphate and evaporated. The product (1.55 g) was isolated by column chromatography of the residue using gradient elution (Kieselgel 1:1 going to 1:2 hexane:ethyl acetate as eluent). $\nu_{max}$(CHCl$_3$) 3400, 1785, 1705 and 1680(s)cm$^{-1}$. $\delta$(CDCl$_3$) 2.17 (3H, s), 3.34 (1H, d, J 18.4Hz), 3.53 (1H, d, J 18.3Hz), 3.61 (1H, d, J 16.2Hz), 3.69 (1H, d, J 16.2Hz), 3.82 (1H, d, J 12.3Hz), 3.92 (1H, d, J 12.3Hz), 4.96 (1H, d, J 4.9Hz), 5.68 (1H, d, J 1.1Hz), 5.76 (1H, d, J 0.8Hz), 5.86 (1H, dd, J 4.9 and 9.0Hz), 6.19 (1H, d, J 9.0Hz), 6.94 (1H, s), 7.2–7.45 (15H, m). [Mass spectrum: +ve ion (3NOBA, Na+) MNa+ 661].

(b) Diphenylmethyl
7β-Amino-3-(6-methyl-2-oxo-2H-pyran-4-ylthiomethyl)ceph-3-em-4-carboxylate A stirred solution of diphenylmethyl 3-(6-methyl-2-oxo-2H-pyran-4-ylthiomethyl)-7β-phenylacetamidoceph-3-em-4-carboxylate (1.55 g) in dichloromethane (20 ml) was cooled to −15° to −20° C. and N-methylmorpholine (0.54 ml) was added followed by a solution of phosphorus pentachloride in dichloromethane (19 ml of a solution containing 40 mg ml$^{-1}$). The mixture was maintained at the same temperature for 0.5 h and then methanol (4.9 ml) was added and the mixture stirred at room temperature for 0.5 h. Water (6.6 ml) was then added and the mixture was vigorously stirred for 0.5 h. Most of the dichloromethane was removed on a rotary evaporator and the residue was stirred with water and ethyl acetate. The pH of the aqueous phase was adjusted to 6.2 with 1N aqueous ammonia. The organic phase was separated, washed with water and brine, dried over magnesium sulphate and evaporated. The product (1.20 g) was isolated by column chromatography using gradient elution (Kieselgel 1:1 hexane:ethyl acetate going to neat ethyl acetate). $\nu_{max}$(CHCl$_3$) 1785, 1710cm$^{-1}$ $\delta$(CDCl$_3$) 1.79 (2H, S). 2.18 (3H, S) 3.42 (1H, d, J 18.2Hz), 3.61 (1H, d, J 18.3Hz), 3.80 (1H, d, J 12.2Hz), 3.90 (1H, d, J 12.2Hz), 4.80 (1H, d, J 5.2Hz), 4.96 (1H, d, J 5.1Hz), 5.66 (1H, d, J ca 1Hz), 5.78 (1H, d, J ca 1Hz), 7.00 (1H, s), 7.2–7.45 (10H, m). [Mass spectrum: +ve ion (3NOBA, Na+) MNa+ 543].

(c) Diphenylmethyl
3-(6-methyl-2-oxo-2H-pyran-4-ylthiomethyl)-7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (470 mg) and N,N-diisopropylethylamine (0.34 ml) in dimethylformamide (4 ml) was cooled to −55° to −60° C. and methanesulphonyl chloride (0.075 ml) was added. The mixture was stirred at the same temperature for 0.5 h and then a solution of diphenymethyl 7β-amino-3-(6-methyl-2-oxo-2H-pyran-4-ylthiomethyl)ceph-3-em-4-carboxylate (450 mg) in dimethylformamide (4 ml) was added, followed by pyridine (0.071 ml). The mixture was stirred at 0° C. for 1.5 h and then partitioned between ethyl acetate and citric acid solution. The organic phase was then washed successively with water, sodium bicarbonate solution, water and brine. The solution was dried over magnesium sulphate and evaporated. The product (576 mg) was isolated by column chromatography of the residue using gradient elution (Kieselgel 1:1 hexane:ethyl acetate going to neat ethyl acetate). $\nu_{max}$(CHCl$_3$) 3400, 1780, 1710 and 1680(s). $\delta$(CDCl$_3$) 2.18 (3H, s), 3.46 (1H, d, J 18.3Hz), 3.61 (1H, d, J 18.4Hz), 3.85 (1H, d, J 12.3Hz), 3.96 (1H, d, J 12.3Hz), 4.08 (3H, s), 5.08 (1H, d, J 4.9Hz), 5.69 (1H, s), 5.78 (1H, s), 5.96 (1H, dd, J 4.9 and 8.9Hz), 6.74 (1H, s), 6.81 (1H, d, J 8.8Hz), 6.97 (1H, s), 7.02 (1H, s), 7.2–7.5 (25H, m). [Mass spectrum: +ve ion (3NOBA, Na+) MNa+ 1196].

(d) Sodium
7β-[2-(2-Aminothiazol-4-yl)-2-(Z)-methoxyiminoacetamido]-3-(6-methyl-2-oxo-2H-pyran-4-ylthiomethyl)ceph-3-em-4-carboxylate Diphenylmethyl 3-(6-methyl-2-oxo-2H-pyran-4-ylthiomethyl)-7β-[2-(2-tritylaminothiazol-4-yl)-2-(Z)-methoxyiminoacetamido]ceph-3-em-4-carboxylate (576 mg) was dissolved in 100% formic acid and 1N hydrochloric acid (0.62 ml) and water (0.62 ml) were then added. The mixture was stirred at room temperature for 0.5 h and then concentrated hydrochloric acid (0.5 ml) was added and the mixture stirred for a further 1 h. The solid was filtered off and the filter cake washed with 90% formic acid. The combined filtrates were evaporated and a 1:1 mixture of tetrahydrofuran and toluene evaporated from the residue twice. The residue was triturated with ether and the ether decanted. The residue was stirred with water and toluene and the pH of the aqueous phase adjusted to 6.2 with sodium bicarbonate solution. The aqueous phase was separated and evaporated and the product isolated by HP20SS chromatography of the residue (water with increasing proportions of acetone as eluent). Fractions containing product were combined and evaporated, dissolved in ca 20 ml water and freeze-dried to give 154 mg of product. $\nu_{max}$(KBr) 1762, 1675, 1617cm$^{-1}$ $\delta$[(CD$_3$)$_2$SO] 2.15 (3H, s), 3.27 (1H, d, J 17.2Hz), 3.52 (1H, d, J 17.2Hz), 3.83 (3H, s), 4.19 (1H, d, J 12.7Hz), 4.31 (1H, d, J 12.7Hz), 5.01 (1H, d, J 4.7Hz), 5.56 (1H, dd, J 4.7 and 8.2Hz), 6.13 (1H, s), 6.26 (1H, s), 6.73 (1H, s), 7.24 (2H, s), 9.55 (1H, d, J 8.2Hz). [Mass spectrum: +ve ion (thioglycerol) MH$^+$ 560].

EXAMPLE 15

Sodium
7β-2-(2-Aminothiazol-4-yl)-2-(Z)-methoxyiminoacetamido]-3-(2-oxo-2H-pyran-4-ylthiomethyl)-ceph-3-em-4-carboxylate (a) Diphenylmethyl
3-(2-Oxo-2H-pyran-4-ylthiomethyl)-7β-phenylacetamidoceph-3-em-4-carboxylate A mixture of 4-hydroxypyranone$^6$ (920 mg) and phosphorus pentasulphide (450 mg) in dry dioxan (30 ml) was heated at 90° C. for 3 hours. Most of the solvent was then removed on a rotary evaporator and the residue partitioned between chloroform and water, and the mixture filtered through Celite to remove solid material. The aqueous phase was extracted with three portions of chloroform and the combined organic phases were washed with brine, dried over magnesium sulphate and evaporated. The product was partially purified by column chromatography (Kieselgel, 4:1 ethyl acetate:acetic acid) to give 566 mg of a red oil. The red oil (256 mg) and diphenylmethyl 3-chloromethyl-7β-phenylacetamidoceph-3-em-4-carboxylate (1.064 gm) were dissolved in dichloromethane (20 ml) and N,N-diisopropylethylamine (0.348 ml) was added to the stirred solution. The mixture was stirred for 1 hour at room temperature and then washed with citric acid solution, water, sodium bicarbonate solution, water and brine, and dried over magnesium sulphate. The solution was evaporated and the product isolated by column chromatography using gradient elution (Kieselgel 3:2 hexane:ethyl acetate going to neat ethyl acetate) to give 326 mg of the desired product. $\nu_{max}$(CHCl$_3$) 3410, 1785, 1720 and 1680cm$^{-1}$. $\delta$H(CDCl$_2$) 3.35 (1H, d, J 18.3Hz), 3.55 (1H, d, J 18.2Hz), 3.61 (1H, d, J16.2Hz), 3.69 (1H, d, J16.5Hz), 3.85 (1H, d, J 12.2Hz), 3.93 (1H, d, J 12.20Hz), 4.97 (1H, d, J 4.9Hz), 5.82 (1H, s), 5.87 (1H, dd, J 4.9 and 9.0Hz), 5.96 (1H, dd, J 1.8, and 5.5Hz), 6.15 (1H, d, J 9.0Hz), 6.95 (1H, s). 7.2-7.45 (16H, m).

(b) Diphenylmethyl
7β-Amino-3-(2-oxo-2H-pyran-4-ylthiomethyl)ceph-3-em-4-carboxylate A stirred solution of dipenylmethyl 3-(2-oxo-2H-pyran-4-ylthiomethyl)-7β-phenylacetamidoceph-3-em-4-carboxylate (326 mg) in dichloromethane (4 ml) was cooled to −15° C. to −20° C., then N-methylmorpholine (0.115 ml) was added followed by a solution of phosphorus pentachloride in dichlormethane (4 ml of a solution containing 40 mg ml$^{-1}$). The mixture was stirred at the same temperature for 30 mins and then methanol (1 ml) was added and the mixture stirred at room temperature for a further 30 mins. Water (1 ml) was then added and the mixture vigorously stirred for 30 mins. Most of the dichloromethane was removed on a rotary evaporator and the residue was stirred with ethyl acetate and water as the pH of the aqueous phase was adjusted to 6.2 with 1N ammonia solution. The organic phase was separated, washed with water and brine, dried over magnesium sulphate and evaporated. The product was isolated by column chromatography of the residue (Kieselgel, EtOAc) to give 160 mg of product. $\nu_{max}$(CHCl$_3$) 1785 and 1720cm$^{-1}$; $\delta$H(CDCl$_3$) 1.84 (2H, br.s), 3.42 (1H, d, J 18.2Hz), 3.61 (1H, d, J 18.2Hz), 3.86 (2H, s), 4.79 (1H, d, J 5.1Hz), 4.94 (1H, d, J 5.00Hz), 5.77 (1H, d, J 0.9Hz), 5.95 (1H, dd, J 1.9 and 5.5Hz), 6.97 (1H, s), 7.2–7.45 (10H, m). [Mass spectrum: +ve ion (3NOBA, Na$^+$) MNa$^+$ 529].

(c) Diphenylmethyl
3-(2-Oxo-2H-pyran-4-ylthiomethyl)-7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (167 mg) in dimethylformamide (1.3 ml) was cooled to −55° to −60° C., and N,N-diisopropylethylamine (0.121 ml) was added followed by methanesulphonyl chloride (0.027 ml). The mixture was stirred at the same temperature for 30 mins and then a solution of diphenylmethyl 7β-amino-3-(2-oxo-2H-pyran-4-ylthiomethyl)ceph-3-em-4-carboxylate (160 mg) in dimethylformamide (2 ml) was added, followed by pyridine (0.026 ml). The mixture was then stirred at 0° C. for 2 hours and then partioned between ethyl acetate and citric acid solution. The organic phase was washed successively with water, sodium bicarbonate solution, three times with water and finally with brine. The solution was dried over magnesium sulphate and evaporated. The product (240 mg) was isolated by column chromatography of the residue (Kieselgel 3:7 hexane ethyl acetate). $\nu_{max}$(CHCl$_3$) 3400, 1795, 1720 and 1690(s)cm$^{-1}$; $\delta$(CDCl$_3$) 3.42 (1H, d, J 18.3Hz), 3.62 (1H, d, J 18.3Hz), 3.88 (1H, d, J 12.2Hz), 3.97 (1H, d, J 12.1Hz), 4.08 (3H, s), 5.08 (1H, d, J 4.8Hz), 5.83 (1H, s), 5.92–6.04 (2H, m), 6.72 (1H, s), 6.86 (1H, d, J 8.7Hz), 6.98 (1H, s), 7.04 (1H, s), 7.2–7.5 (25H, m).

(d) Sodium
7δ-[2-(2-Aminothiazol-4-yl)-2-(Z)-methoxyiminoacetamido]-3-(2-oxo-2H-pyran-4-ylthiomethyl)-ceph-3-em-4-carboxylate Diphenylmethyl 3-(2-oxo-2H-pyran-4-ylthiomethyl)-7β[-2-(2-tritylaminothiazolyl-4-yl)-2-(Z)-methoxyiminoacetamido]ceph-3-em-4-carboxylate (240 mg) was dissolved in 98% formic acid and then 1N hydrochloric acid (0.24 ml) was added. The mixture was stirred at room temperature for 30 mins and then concentrated hydrochloric acid (0.19 ml) was added. After stirring for a further hour the solid was filtered off and washed with 90% formic acid. The combined filtrates were evaporated and toluene evaporated from the residue twice. The residue was stirred with water and toluene and the pH of the aqueous phase was adjusted to 6.2 with sodium bicarbonate solution. The aqueous phase was separated and evaporated to ca 2 ml and the product isolated by HP20SS chromatography using water with increasing proportions of acetone as eluent. Fractions containing product were combined, evaporated, dissolved in water (10 ml) and freeze-dried to yield 48 mg of product. $v_{max}$(KBr) 1762, 1670, 1611cm$^{-1}$; $\delta$[(CD$_3$)$_2$SO] 3.29 (1H, d, J 17.3Hz), 3.53 (1H,d, J 17,3Hz), 3.83 (3H, s), 4.25 (1H, d, J 12.8Hz), 4.32 (1H, d, J 12.8Hz), 5.02 (1H, d, J 4.7Hz) 5.56 (1H, dd, J 4.8 and 8.1Hz), 6.31 (1H, s), 6.40 (1H, dd, J 1.6 and 5.6Hz), 6.73 (1H, s), 7.25 (2H, s), 7.61 (1H, d, J 5.6Hz), 9.56 (1H, d, J 8.1Hz). [Mass spectrum: +ve ion (thioglycerol) MH+ 546].

EXAMPLE 16

7β-2-(2-Aminothiazol-4-yl)-2-(Z)-carboxymethoxyiminoacetamido]-3-(2,5-dihydro-2-oxofuran-4-ylthiomethyl)ceph-3-em-4-carboxylic acid, disodium salt (a) Diphenylmethyl 3-(2,5-Dihydro-2-oxofuran-4-ylthiomethyl)-7β-[2-(2-tritylaminothiazol-4-yl)-2-(Z)-(t-butyloxycarbonyl)methoxyiminoacetamido]ceph-3-em-4-carboxylate A stirred solution of 2-(2-tritylaminothiazol-4-yl)-2-(Z)-(t-butyloxycarbonyl)methoxyiminoacetic acid (498 mg) in dimethylformamide (4 ml) was cooled to −55° C. to −60° C. and N,N-diisopropylethylamine (0.157 ml) was added, followed by methanesulphonyl chloride (0.068 ml). The mixture was stirred at the same temperature for 0.5 h and then diphenylmethyl 7β-amino-3-(2,5-dihydro-2-oxofuran-4-ylthiomethyl)ceph-3-em-4-carboxylate (395 mg) and pyridine (0.064 ml) were added. The mixture was then stirred at 0° for 1.25 h, and then partitioned between ethyl acetate and citric acid solution. The organic phase was washed successively with water, sodium bicarbonate solution, water and brine. The solution was dried over magnesium sulphate and evaporated. The product (567 mg) was isolated by column chromatography of the residue using gradient elution (Kieselgel 1:1 going to 3:7 hexane: ethyl acetate as eluent). $v_{max}$(CHCl$_3$) 3400, 3250, 1790, 1745, 1730 and 1680cm$^{-1}$; $\delta$(CDCl$_3$) 1.43 (9H, s), 3.40 (1H, d, J 18.0Hz), 3.56 (1H, d, J 18.0Hz), 3.91 (1H, d, J 12.4Hz), 4.02 (1H, d, J 12.4Hz), 4.72 (2H, s), 4.73 (1H, d, J 17.1Hz), 4.81 (1H, d, J 17.1Hz), 5.08 (1H, d, J 4.9Hz), 5.66 (1H, s), 5.93 (1H, dd, J 4.9 and 8.3Hz), 6.82 (1H, s), 6.95 (1H, s,), 7.01 (1H, s), 7.2–7.45 (25H, m), 8.77 (1H, d, J 8.3Hz).

(b) 7β-[2-(2-Aminothiazol-4-yl)-2-(Z)-carboxymethoxyiminoacetamido]-3-(2,5-dihydro-2-oxofuran-4-ylthiomethyl)ceph-3-em-4-carboxylic acid, disodium salt Diphenylmethyl 3-(2,5-dihydro-2-oxofuran-4-ylthiomethyl)-7β-[2-(2-tritylaminothiazol-4-yl)-2-(Z)-(t-butyloxycarbonyl)methoxyiminoacetamido]ceph-3-em-4-carboxylate (623 mg) was dissolved in 100% formic acid (12 ml) and 1N hydrchloric acid (0.61 ml) and water (0.61 ml) were added. The mixture was stirred at room temperature for 0.5 h and then concentrated hydrochloric acid (0.48 ml) was added. The mixture was stirred for 1 h and then the solid was filtered off and washed with 90% formic acid. The combined filtrates were evaporated and the residue partitioned between toluene and water. The pH of the aqueous phase was adjusted to 6.2 with sodium bicarbonate solution, the mixture was filtered and the aqueous phase separated and evaporated. The product was isolated by HP20SS chromatography of the residue (water with increasing proportions of acetone as eluent). Fractions containing product were combined and evaporated. The residue was dissolved in water (ca 20 ml) and freeze-dried to give the product (161 mg). $v_{max}$(KBr) 1760, 1734 and 1603cm$^{-1}$; $\delta$(CD$_3$)$_2$SO] 3.23 (1H, d, J 17.1Hz), 3.50 (1H, d, J 17.2Hz), 4.10 (1H, d, J 13.1Hz), 4.25 (2H, s), 4.35 (1H, d, J 13.1Hz), 4.94 (2H, s), 5.00 (1H, d, J 4.9Hz), 5.61 (1H, dd, J 4.9 and 8.6Hz), 6.27 (1H, s), 6.83 (1H, s), 7.22 (2H, s), 11.74 (1H, d, J 8.6Hz). [Mass spectrum: +ve ion (thioglycerol) MH+ 600].

EXAMPLE 17

7β-[2-(2-Aminothiazol-4-yl)-2-(Z)-hydroxyiminoacetamido]-3-(6-methyl-2-oxo-2H-pyran-4-ylthiomethyl)ceph-3-em-4-carboxylic acid (a) Diphenylmethyl 3-(6-Methyl-2-oxo-2H-pyran-4-ylthiomethyl)-7β-[2-(2-tritylaminothiazol-4-yl)-2-(Z)-trityloxyiminoacetamido]ceph-3-em-4-carboxylate A stirred solution of sodium 2-(2-tritylaminothiazol-4-yl)-2-(Z)-trityloxyiminoacetate (1.05 g) in dimethylformamide (5.5 ml) was cooled to −55° to −60° C. and methanesulphonyl chloride (0.117 ml) was added. The mixture was stirred at the same temperature for 0.5 h and then a solution of diphenylmethyl 7β-amino-3-(6-methyl-2-oxo-2H-pyran-4-ylthiomethyl)ceph-3-em-4-carboxylate (699 mg) in dimethylformamide (4 ml) and pyridine (0.11 ml) were added. The mixture was then stirred at 0° C. for 1.5 h. The mixture was partitioned between ethyl acetate and citric acid solution, and the organic phase was washed successively with water, sodium bicarbonate solution, twice with water and finally with brine. The solution was dried over magnesium sulphate and evaporated. Column chromatography of the residue using gradient elution (Kieselgel 2:1 going to 1:1 hexane:ethyl acetate) gave the product (969 mg). $v_{max}$(CHCl$_3$) 3400, 1790 and 1710cm$^{-1}$; $\delta$(CDCl$_3$) 2.17 (3H, s), 3.24 (1H, d, J 18.3Hz), 3.51 (1H, d, J 18.3Hz), 3.90 (2H, s), 5.07 (1H, d, J 5.0Hz), 5.68 (1H, s), 5.77 (1H, s), 6.09 (1H, dd, J 5.0 and 9.0Hz), 6.42 (1H, s), 6.75 (1H, s), 6.98 (1H, s), 7.15–7.5 (41H, m).

(b) 7β-[2-(2-Aminothiazol-4-yl)-2-(Z)-hydroxyiminoacetamido]-3-(6-methyl-2-oxo-2H-pyran-4-ylthiomethyl)ceph-3-em-4-carboxylic Acid Diphenylmethyl 3-(6-methyl-2-oxo-2H-pyran-4-ylthiomethyl)-7β-[2-(2-tritylaminothiazol-4-yl)-2-(Z)-trityloxyiminoacetamido]ceph-3-em-4-carboxylate (969 mg) was dissolved in 100% formic acid (14.9 ml) and 1N hydrochloric acid (0.825 ml) and water (0.825 ml) were added. The mixture was stirred at room temperature for 0.5 h and then concentrated hydrochloric acid (0.66 ml) was added. The mixture was stirred for 1 h and then the solid was filtered off and washed with 90% formic acid. The combined filtrates were evaporated and a 1:1 mixture of toluene and tetrahydrofuran was evaporated from the residue twice. The residue was triturated with ether and the solid filtered off and washed with ether. The solid was suspended in water and the pH adjusted to 2.6 with 0.1N sodium hydroxide solution. The resulting solid was filtered off, washed with water and dried under vacuum to give the product. $v_{max}$(KBr) 1773, 1675 and 1624cm$^{-1}$; $\delta$[(CD$_3$)$_2$SO] 2.16 (3H, s), 3.47 (1H, d, J 17.9Hz), 3.70 (1H, d, J 18.0Hz), 4.11 (1H, d, J 12.9Hz), 4.19 (1H, d, J 13.1Hz), 5.18 (1H, d, J 4.8Hz), 5.79 (1H, dd, J 4.8 and 8.2Hz), 6.00 (1H, s), 6.21 (1H, s), 6.66 (1H, s), 7.17 (2H, s), 9.48 (1H, s).

EXAMPLE 18

Pivaloyloxymethyl 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate Sodium iodide (120 mg) was added to a stirred solution of pivaloyloxymethyl bromide (80 mg) in acetone (2 ml). The mixture was stirred in the dark for 10 minutes and then filtered through Celite. The solvent was evaporated and the residue triturated with toluene. The solution was filtered into a solution of sodium 7β-[2-(2-aminothiazol-4-yl)-2-(Z)-methoxyiminoacetamido]-3-(2,5-dihydro-2-oxofuran-4-ylthiomethyl)ceph-3-em-4-carboxylate (175 mg) in N-methylpyrrolidinone (5 ml). The mixture was stirred at room temperature for 1 h and then partitioned between ethyl acetate and water. The organic phase was separated and washed with four portions of water, then brine, dried over magnesium sulphate and evaporated. Column chromatography of the residue (Kieselgel, ethyl acetate as eluent) gave the product (151 mg). $\nu_{max}$(CHCl$_3$) 3480, 3400, 3340, 1780, 1745 and 1680cm$^{-1}$; δ(CDCl$_3$) 1.23 (9H, s), 3.52 (1H, d, J 18.3Hz), 3.65 (1H, d, J 18.3Hz), 4.01 (1H, d, J 13.1Hz), 4.06 (3H, s), 4.23 (1H, d, J 13.0Hz), 4.82 (2H, s), 5.13 (1H, d, 4.9Hz), 5.53 (2H, s), 5.84 (1H, s), 5.90 (1H, d, J 5.8Hz), 5.93 (1H, d, J 5.7Hz), 6.09 (1H, dd, J 4.9 and 9.0Hz), 6.77 (1H, s), 7.27 (1H, s), 7.90 (1H, d, J 8.9Hz).

The following esters were prepared by the same method.

EXAMPLE 19

Pivaloyloxymethyl 7β-[2-(2-Aminothiazol-4-yl)-2-(Z)-methoxyiminoacetamido]-3-(2,5-dihydro-2-oxofuran-4-ylthio)ceph-3-em-4-carboxylate Sodium 7β-[2-(2-aminothiazol-4-yl)-2-(Z)-methoxyiminoacetamido]-3-(2,5-dihydro-2-oxofuran-4-ylthio)ceph-3-em-4-carboxylate (159 mg) gave 88 mg of the pivaloyloxymethyl ester. $\nu_{max}$(CHCl$_3$) 3480, 3400, 3330, 1780, 1745 and 1680cm$^{-1}$; δ(CDCl$_3$) 1.22 (9H, s), 3.49 (1H, d, J 18.3Hz), 3.80 (1H, d, J 18.3Hz), 4.06 (3H, s), 4.81 (1H, d, J 16.6Hz), 4.90 (1H, d, J 16.7Hz), 5.21 (1H, d, J 5.2Hz), 5.63 (2H, s), 5.83 (1H, s), 5.85 (1H, d, J 5.8Hz), 5.93 (1H, d, J 5.6Hz), 6.08 (1H, dd, J 5.1Hz and 8.7Hz), 7.65 (1H, d, J 8.7Hz).

EXAMPLE 20

Pivaloyloxymethyl 7β-[2-(2-Aminothiazol-4-yl)-2-(Z)-methoxyiminoacetamido]-3-(3-chloro-2,5-dihydro-2-oxofuran-4-ylthiomethyl)ceph-3-em-4-carboxylate Sodium 7β-[2-(2-aminothiazol-4-yl)-2-(Z)-methoxyiminoacetamido]-3-(3-chloro-2,5-dihydro-2-oxofuran-4-ylthiomethyl)ceph-3-em-4-carboxylate (79 mg) gave 51 mg of the pivaloyloxymethyl ester. $\nu_{max}$(CHCl$_3$) 3480, 3390, 3320, 1770 and 1675cm$^{-1}$; δ(CDCl$_3$) 1.23 (9H, s), 3.57 (1H, d, J 18.4Hz), 3.67 (1H, d, J 18.4Hz), 4.06 (3H, s), 4.10 (1H, d, J 13.1Hz), 4.27 (1H, d, J 13.1Hz), 4.96 (2H, s), 5.14 (1H, d, J 5.0Hz), 5.45 (2H, s), 5.90 (1H, s), 6.07 (1H, dd, J 4.9Hz and 8.9Hz), 6.81 (1H, s), 7.76 (1H, d, J 8.9Hz).

EXAMPLE 21

Pivaloyloxymethyl 7β-[2-(2-Aminothiazol-4-yl)-2-(Z)-methoxyiminoacetamido]-3-(2-oxo-2H-pyran-4-ylthiomethyl)-ceph-3-em-4-carboxylate Sodium 7β-[2-(2-aminothiazol-4-yl)-2-(Z)-methoxyiminoacetamido]-3-(2-oxo-2H-pyran-4-ylthiomethyl)-ceph-3-em-4-carboxylate (137 mg) gave 75 mg of the pivaloyloxymethyl ester. $\nu_{max}$(CHCl$_3$) 3490, 3400, 3330, 1785, 1720 and 1680cm$^{-1}$; δ(CDCl$_3$) 1.22 (9H, s), 3.51 (1H, d, J 18.35Hz), 3.67 (1H, d, J 18.43), 4.0–4.1 (2H, m), 4.06 (3H, s), 5.12 (1H, d, J 4.92Hz), 5.8–6.1 (3H, m), 5.88 (1H, d, J 5.59Hz), 5.95 (1H, d, J 5.52Hz), 6.00 (1H, s), 6.07 (1H, dd, J 1.82 and 6.45Hz), 6.82 (1H, s), 7.34 (1H, d, J 5.62Hz), 7.89 (1H, d, J 8.86Hz).

EXAMPLE 22

Sodium 7β-[2-(2-Aminothiazol-4-yl)-2-(Z)-methoxyiminoacetamido]-3-(2,5-dihydro-2-oxofuran-4-ylmethyloxy)ceph-3-em-4-carboxylate (a) Diphenylmethyl 3-(2,5-Dihydro-2-oxofuran-4-ylmethyloxy)-7β-phenylacetamidoceph-3-em-4-carboxylate Diphenylmethyl-3-hydroxy-7β-phenylacetamidoceph-3-em-4-carboxylate (250 mg), 2,5-dihydro-3-hydroxymethylfuran-2-one[7] (68 mg), and triphenylphosphine (131 mg) were dissolved in dry tetrahydrofuran (5 ml) under an inert atmosphere. Diethylazodicarboxylate (94 μl) was added and the reaction then stirred at room temperature for 2 h. The solvent was removed by evaporation in vacuo and then redissolved in dichloromethane. The solution was purified by chromatography on silica gel (Keiselgel) using gradient elution (3:7 ethyl acetate/hexane rising to 7:3 ethyl acetate/hexane). Chromatography was repeated under identical conditions giving the title compound which was finally isolated as a foam (202 mg). $\nu_{max}$(CH$_2$Cl$_2$) 3420, 1785, 1755, and 1690cm$^{-1}$; δH(CDCl$_3$) 2.89 (1H, d, J 16.0Hz), 3.28 (1H, d, J 16.3Hz), 3.60–3.74 (2H, m), 4.52–4.63 (4H, m), 5.02 (1H, d, J 4.12Hz), 5.63 (1H, dd, J 8.4Hz, 4.15Hz), 5.96 (1H, s), 6.64 (1H, d, J 8.4Hz), 6.82 (1H, s), and 7.27–7.57 (15H, m).

(b) Diphenylmethyl 7β-Amino-3-(2,5-dihydro-2-oxofuran-4-ylmethyloxy)-ceph-3-em-4-carboxylate Diphenylmethyl 3-(2,5-dihydro-2-oxofuran-4-ylmethyl oxy)-7β-phenylacetamidoceph-3-em-4-carboxylate (958 mg) was dissolved in dichloromethane (13 ml) whilst under an inert atmosphere. The solution was cooled to −20° C. before treating with N-methylmorpholine (352 μl) followed by a solution of phosphorous pentachloride in dichloromethane (12.5 ml of 40 mg ml$^{-1}$ solution). After stirring for 30 min. at −20° C. the solution was treated with methanol (3.2 ml) and then allowed to warm to RT. After a further 30 min. water (4.3 ml) was added and the reaction was stirred vigorously for 60 min. Solvent was removed by evaporation in vacuo and the residue dissolved in ethyl acetate/water. The pH of the mixture was adjusted to 6.5 with 1.0M aqueous ammonia. Separation of the organic phase was followed by washing with water and brine before drying over anhydrous magnesium sulphate.

Purification was accomplished by chromatography of the crude material on silica gel (Keiselgel) eluting with ethyl acetate. The title compound was finally isolated as a foam (565 mg). $\nu_{max}(CH_2Cl_2)$ 1780, 1755 and 1730cm$^{-1}$; $\delta H(CDCl_3)$ 3.34 (1H, d, J 17.7Hz), 3.54 (1H, d, J 17.7Hz), 4.51–4.58 (2H, m), 4.70 (2H, bs) 4.75 (1H, d, J 4.7Hz), 4.97 (1H, d, J 4.7Hz), 5.93 (1H, s), and 7.26–7.40 (10H, m). [Mass spectrum: FAB +ve ion (3NOBA/Na+) MNa+ 501].

(c) Diphenylmethyl 3-(2,5-Dihydro-2-oxofuran-4-ylmethyloxy)-7β-[2-(2-tritylaminothiazol-4-yl)-2-(Z)-methoxyiminoacetamido]ceph-3-em-4-carboxylate A stirred solution of 2-(2-tritylaminothiazol-4-yl)-2-(Z)-methoxyiminoacetic acid hydrochloride (300 mg) in dimethylformamide (4 ml) was cooled to $-50°$ C. whilst under an inert atmosphere. N,N-Diisopropylethylamine (218 μl) was added followed by methanesulphonyl chloride (49 μl). The reaction was stirred for 30 min. at $-50°$ C. before treating with pyridine (52 μl) followed by a solution of diphenylmethyl 7β-amino-3-(2,5-dihydro-2-oxofuran-4-ylmethyloxy)ceph-3-em-4-carboxylate (300 mg) in dimethylformamide (4 ml) and the temperature allowed to rise to 0° C. The reaction was stirred for 15 min. and then poured into ethyl acetate and water. The organic phase was washed with water (two times) and brine before drying over anhydrous magnesium sulphate. Chromatography on silica gel (Keiselgel) eluting with 4:1 ethyl acetate/hexane gave the title compound which was finally isolated as a foam (431 mg). $\nu_{max}(CH_2Cl_2)$ 3400, 1785, 1755, and 1730cm$^{-1}$; $\delta H(CDCl_3)$ 3.34 (2H, s), 4.08 (3H, s), 4.64 (2H, s) 4.73 (2H, bs), 5.11 (1H, d, J 4.5Hz), 5.79 (1H, dd, J 8.24Hz, 4.5Hz), 5.95 (1H, bs) 6.77 (1H, s), 6.90 (1H, s), 6.96 (1H, d, J 8.07Hz), 7.02 (1H, s), and 7.26–7.39 (25H, m). [Mass spectrum: FAB +ve ion (3NOBA/Na+)MH+ 904, MNa+ 926].

(d) Sodium 7β-[2-(2-Aminothiazol-4-yl)-2-(Z)-methoxyiminoacetamido]-3-(2,5-dihydro-2-oxofuran-4-ylmethyloxy)ceph-3-em-4-carboxylate Diphenylmethyl 3-(2,5-dihydro-2-oxofuran-4-ylmethyloxy)-7β-[2-(2-tritylaminothiazol-4-yl)-2-(Z)-methoxyiminoacetamido]ceph-3-em-4-carboxylate (394 mg) was completely dissolved in 98–100% formic acid (4.4 ml) before treating with 1.0M hydrochloric acid (440 μl). The reaction was stirred at room temperature for 30 min. and then treated with one drop of concentrated hydrochloric acid. Stirring was continued for 30 min. Any solid was removed by filtration and the filter cake washed with a small amount of 90% formic acid. The filtrate was evaporated to dryness and toluene evaporated from the residue (three times). The residue was dissolved in ethyl acetate/water and the pH adjusted up to 6.5 with saturated sodium bicarbonate solution. After separating the aqueous phase it was evaporated to low volume and chromatographed on HP20SS resin eluting with water containing an increasing proportion of tetrahydrofuran. The aqueous mixture containing the product was evaporated to low volume and freeze dried to give the title compound as a white solid (134 mg). $\nu_{max}$(KBr disc) 1744 and 1605cm$^{-1}$; $\delta H(D_2O)$ 3.40 (1H, d, J 17.2Hz), 3.69 (1H, d, J 17.2Hz), 3.92 (3H, s), 4.88 (1H, s), 4.91 (1H, s) 4.98 (2H, s), 5.16 (1H, d, J 4.4Hz), 5.64 (1H, d, J 4.4Hz), 6.13 (1H, s), and 6.99 (1H, s). [Mass spectrum: FAB +ve ion (thioglycerol) MH+ 518].

References

1 : Helv. Chim. Acta., 59(8), 2724–7, 1976
2 : Tetrehedron Lett., 31. 4227–8, 1990
3 : Annali di Chimica, 63, 269, 1973
4 : Helv. Chim. Acta., 59(1), 100–7, 1976
5 : EPA-0 153,615
6 : Chem. Ber., 118, 741, 1982
7 : J. Chem. Res.(s), 222–3, 1986

| | In Vitro Biological Data MIC (μg/ml) | |
|---|---|---|
| | Organism | |
| Example No. | E. coli (NCTC 10418) | S. aureus (Oxford) |
| 1 | <0.03 | 0.25 |
| 2 | 0.12 | 1.0 |
| 3 Isomer (a) | 0.5 | 4 |
| Isomer (b) | 0.12 | 4 |
| 4 | 0.25 | 1.0 |
| 5 | <0.03 | 0.25 |
| 6 | <0.03 | 0.12 |
| 7 | <0.03 | 0.5 |
| 8 | 0.12 | 0.25 |
| 9 | 0.12 | 2.0 |
| 12 | 0.12 | 0.25 |
| 13 | <0.03 | 0.25 |
| 14 | <0.03 | 0.5 |
| 15 | <0.03 | 0.25 |
| 16 | <0.06 | 8 |
| 17 | 0.06 | 0.25 |
| 22 | 0.06 | 2.0 |

We claim:
1. A compound of formula (I) or a pharmaceutically acceptable salt thereof:

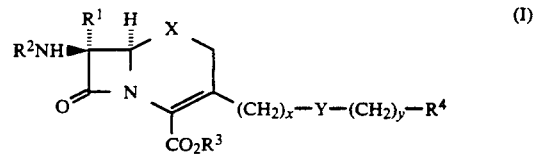

wherein
R$^1$ is hydrogen, methoxy or formamido;
R$^2$ is an acyl group selected from the group consisting essentially of:

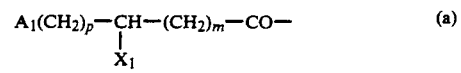

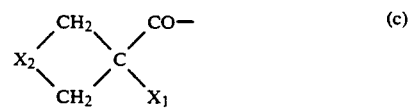

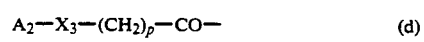

and

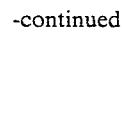
(e)

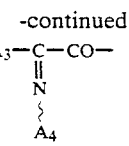
(f)

wherein p is 0, 1 or 2; m is 0, 1 or 2; $A_1$ is $C_{1-6}$ alkyl, $C_{3-6}$ cycloalkyl, cyclohexenyl, cyclohexadienyl, hydroxyphenyl, thienyl, pyridyl, thiazolyl, $C_{1-6}$ alkylthio, $C_{1-6}$ alkyloxy or phenyl substituted with up to five groups selected from halogen, mercapto, $C_{1-6}$ alkyl, phenyl, $C_{1-6}$ alkoxy, hydroxy ($C_{1-6}$) alkyl, mercapto ($C_{1-6}$) alkyl, halo ($C_{1-6}$) alkyl, hydroxy, amino, nitro, carboxy, $C_{1-6}$ alkylcarbonyloxy, alkoxycarbonyl, formyl or $C_{1-6}$ alkylcarbonyl; $X_1$ is a hydrogen or halogen atom, a carboxylic acid, carboxylic ester, sulphonic acid, azido, tetrazolyl, hydroxy, acyloxy, amino, ureido, acylamino, quanidino or acylureido group, or heterocyclylamino having 5 or 6 ring atoms and up to four heteroatoms in the ring wherein the heteroatoms are selected from the group consisting of oxygen, nitrogen and sulphur; $A_2$ is phenyl, 2, 6-dimethoxyphenyl, 2-alkoxy-1-naphthyl, 3-arylisoxazolyl or 3-aryl-5-methylsoxaloyl wherein said aryl is phenyl or naphthyl, a substituted alkyl or substituted dithietane; $X_2$ is a —CH$_2$OCH$_2$— or alkylene group; $X_3$ is an oxygen or sulphur atom; $A_3$ is an unsubstituted phenyl or naphthyl or phenyl or naphthyl substituted with up to five groups selected from halogen, mercapto, $C_{1-6}$ alkyl, phenyl, $C_{1-6}$ alkoxy, hydroxy($C_{1-6}$)alkyl, mercapto($C_{1-6}$)alkyl, halo($C_{1-6}$)alkyl, hydroxy, amino, nitro, carboxy, $C_{1-6}$ alkyl carbonyloxy, alkoxycarbonyl, formyl or $C_{1-6}$ alkylcarbonyl groups, or $A_3$ is a heteroaromatic heterocyclic ring or ring system having 5 6 ring atoms and up to four heteroatoms in the ring wherein the heteroatoms are selected from the group consisting of oxygen, nitrogen and sulphur; and $A_4$ is hydrogen, $C_{1-6}$ alkyl, $C_{3-8}$ cycloalkyl, $C_{3-8}$cycloalkyl($C_{1-6}$)alkyl, $C_{1-6}$ alkoxy carbonyl($C_{1-6}$)alkyl, $C_{2-6}$ alkenyl, carboxy($C_{1-6}$)alkyl, $C_{2-6}$ alkynyl, phenyl, naphthyl or $C_{1-6}$ alkyl substituted by up to three phenyl or naphthyl groups; and further, $R^3$ is hydrogen, or a readily removable carboxy protecting group including a pharmaceutically acceptable in-vivo hydrolyzable ester group; $R^4$ is a γ-lactone ring or δ-lactone ring containing zero, one or two endocyclic double bonds, which ring is unsubstituted or substituted at any carbon atom by alkyl, dialkylamino, alkoxy, hydroxy, halogen, phenyl or naphthyl, which in the case of more than one substituent may be the same or different, or is di-substituted at two adjacent carbon atoms, which are available for substitution, to from an aromatic fused bicyclic system wherein one ring is a 5- or 6-membered lactone ring and the other ring is a 5- or 6-membered carbocyclic ring; x and y are independently 0 or 1; X is S, SO or $SO_2$; and Y is O is S.

2. A compound according to claim 1 in which $R^1$ is hydrogen.

3. A compound according to claim 1 in which $R^2$ is an acyl group of said formula (a) or (e):

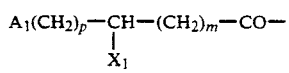
(a)

4. A compound according to claim 3 in which $A_3$ is aminothiazolyl in which the amino group is optionally protected and $A_4$ is hydrogen, $C_{1-6}$alkyl, $C_{1-6}$alkoxycarbonyl($C_{1-6}$)alkyl, carboxy($C_{1-6}$) alkyl or triphenylmethyl.

5. A compound according to claim 1 in which X is S or SO.

6. A compound according to claim 1 in which $R^4$ is 2,5-dihydro-2-oxofuranyl, 2-oxotetrahydrofuranyl, or 2-oxo-2H-pyranyl wherein the furan or pyran ring is optionally substituted by $C_{1-6}$ alkyl or halogen.

7. A compound according to claim 1 in which Y is sulphur; x is 0 and y is 1, or x is 1 and y is 0.

8. A compound of formula (Ia) or a pharmaceutically acceptable salt or in vivo hydrolysable ester thereof:

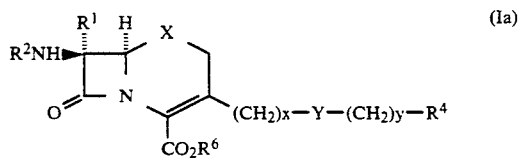
(Ia)

wherein
$R^1$, $R^2$, $R^4$, X, Y, x and y are as defined with respect to formula (I) in claim 1 and the group $CO_2R^6$ is $CO_2R^3$ where $CO_2R^3$ is a carboxy group.

9. A compound according to claim 8 in which the group $CO_2R^6$ is an in vivo hydrolysable pivaloyloxymethyl ester group.

10. A compound of formula (Ia) or a pharmaceutically acceptable salt or in vivo hydrolysable ester thereof as defined in claim 8, selected from the group comprising:
Sodium 7β-[2-(2-Aminothiazol-4-yl)-2-(Z)-methoxyiminoacetamido]-3-(2,5-dihydro-2-oxofuran-4-ylmethylthio)ceph-3-em-4-carboxylate;
Sodium 7β-[2-(2-Aminothiazol-4-yl)-2-(Z)-methoxyiminoacetamido]-3-(2,5-dihydro-2-oxofuran-4-ylthio)ceph-3-em-4-carboxylate;
Sodium 7β-[2-(2-Aminothiazol-4-yl)-2-(Z)-methoxyiminoacetamido]-3-(2,5-dihydro-3-methyl-2-oxofuran-5-yloxy)ceph-3-em-4-carboxylate;
Sodium 7β-[2-(2-Aminothiazol-4-yl)-2-(Z)-methoxyiminoacetamido]-3-(6-methyl-2-oxo-2H-pyran-4-ylthio)ceph-3-em-4-carboxylate:
Sodium 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate;
7β-[2-(2-Aminothiazol-4-yl)-2-(Z)-hydroxyiminoacetamido]-3-(2,5-dihydro-2-oxofuran-4-ylthiomethyl)ceph-3-em-4-carboxylic acid;
Sodium 7β-[2-(2-Aminothiazol-4-yl)-2-(Z)-methoxyiminoacetamido]-3-(2,5-dihydro-2-oxofuran-3-ylmethylthio)ceph-3-em-4-carboxylate;
7β-[2-(2-Aminothiazol-4-yl)-2-(Z)-hydroxyiminoacetamido]-3-(2,5-dihydro-2-oxofuran-3-ylmethylthio)ceph-3-em-4-carboxylic acid;
Sodium 7β-[2-(2-Aminothiazol-4-yl)-2-(Z)-methoxyiminoacetamido]-3-(2-oxotetrahydrofuran-3-ylthio)-ceph-3-em-4-carboxylate;

Pivaloyloxymethyl-7β-[2-(2-Aminothiazol-4-yl)-2-(Z)-methoxyiminoacetamido]-3-(2,5-dihydro-2-oxofuran-3-yl-methylthio)ceph-3-em-4-carboxylate;

Pivaloyloxymethyl 7β-[2-(2-Aminothiazol-4-yl)-2-(Z)-methoxyiminoacetamido]-3-(2-oxotetrahydrofuran-3-ylthio)ceph-3-em-4-carboyxlate;

7β-[2-(2-Aminothiazol-4-yl)-2-(Z)-hydroxyiminoacetamido]-3-(2,5-dihydro-2-oxofuran-4-ylmethylthio)ceph-3-em-4-carboxylic acid;

Sodium 7β-[2-(2-Aminothiazol-4-yl)-2-(Z)-methoxyiminoacetamido]-3-(3-chloro-2,5-dihydro-2-oxofuran-4-ylthiomethyl)ceph-3-em-4-carboxylate;

Sodium 7β-[2-(2-Aminothiazol-4-yl)-2-(Z)-methoxyiminoacetamido]-3-(6-methyl-2-oxo-2H-pyran-4-ylthiomethyl)ceph-3-em-4-carboxylate;

Sodium 7β-[2-(2-Aminothiazol-4-yl)-2-(Z)-methoxyiminoacetamido]-3-(2-oxo-2H-pyran-4-ylthiomethyl)ceph-3-em-4-carboxylate;

7β-[2-(2-Aminothiazol-4-yl)-2-(Z)-carboxymethoxyiminoacetamido]-3-(2,5-dihydro-2-oxofuran-4-ylthiomethyl)ceph-3-em-4-carboxylic acid, disodium salt;

7β-[2-(2-Aminothiazol-4-yl)-2-(Z)-hydroxyiminoacetamido]-3-(6-methyl-2-oxo-2H-pyran-4-ylthiomethyl)ceph-3-em-4-carboxylic acid;

Pivaloyloxymethyl 7β-[2-(2-Aminothiazol-4-yl)-2-(Z)-methoxyiminoacetamido]-3-(2,5-dihydro-2-oxofuran-4-ylthiomethyl)ceph-3-em-4-carboxylate;

Pivaloyloxymethyl 7β-[2-(2-Aminothiazol-4-yl)-2-(Z)-methoxyiminoacetamido]-3-(2,5-dihydro-2-oxofuran-4-ylthio)ceph-3-em-4-carboxylate;

Pivaloyloxymethyl 7β-[2-(2-Aminothiazol-4-yl)-2-(Z)-methoxyiminoacetamido]-3-(3-chloro-2,5-dihydro-2-oxofuran-4-ylthiomethyl)ceph-3-3-em-4-carboxylate;

Pivaloyloxymethyl 7β-[2-(2-Aminothiazol-4-yl)-2-(Z)-methoxyiminoacetamido]-3-(2-oxo-2H-pyran-4-ylthiomethyl)ceph-3-em-4-carboxylate; and Sodium 7β-[2-(2-Aminothiazol-4-yl)-2-(Z)-methoxyiminoacetamido]-3-(2,5-dihydro-2-oxofuran-4-ylmethyloxy)ceph-3-em-4-carboxylate.

11. A pharmaceutical composition comprising a compound of formula (Ia) or a pharmaceutically acceptable salt or in vivo hydrolysable ester thereof, as defined in claim 8 and a pharmaceutically acceptable carrier.

12. A pharmaceutical composition according to claim 11 further comprising a β-lactamase inhibitor.

13. A method of treating bacterial infections in humans and animals comprising the administration to a patient of a therapeutically effective amount of a compound of formula (Ia) or a pharmaceutically acceptable salt or in vivo hydrolysable ester thereof, as defined in claim 8.

* * * * *